United States Patent [19]

Nakao et al.

[11] Patent Number: 5,759,187
[45] Date of Patent: Jun. 2, 1998

[54] SURGICAL RETRIEVAL ASSEMBLY AND ASSOCIATED METHOD

[75] Inventors: Naomi L. Nakao; Peter J. Wilk, both of New York, N.Y.

[73] Assignee: Wilk & Nakao Medical Technology, Incorporated, New York, N.Y.

[21] Appl. No.: 333,363

[22] Filed: Nov. 2, 1994

Related U.S. Application Data

[63] Continuation-in-part of Ser. No. 213,196, Mar. 14, 1994, Pat. No. 5,486,182, and Ser. No. 957,416, Oct. 5, 1992, Pat. No. 5,374,273, said Ser. No. 213,196, is a continuation-in-part of Ser. No. 12,657, Feb. 1, 1993, Pat. No. 5,336,227, which is a continuation-in-part of Ser. No. 788,035, Nov. 5, 1991, Pat. No. 5,201,740, and Ser. No. 892,214, Jun. 2, 1992, Pat. No. 5,190,542.

[51] Int. Cl.[6] ............................ A61B 17/24; A61B 17/26
[52] U.S. Cl. ............................ 606/114; 606/113; 606/110
[58] Field of Search ........................... 606/113, 114, 606/21, 2, 24, 14, 110, 127, 47, 41, 32; 604/21, 52; 600/104

[56] References Cited

U.S. PATENT DOCUMENTS

| | | | |
|---|---|---|---|
| 404,946 | 6/1889 | Andersson | 43/11 |
| 460,940 | 10/1891 | Baugh | 606/106 |
| 1,585,483 | 5/1926 | Freer | 43/7 |

(List continued on next page.)

FOREIGN PATENT DOCUMENTS

| | | | |
|---|---|---|---|
| 0025796 | 1/1884 | Brazil | 606/127 |
| 0046856 | 5/1889 | Germany | 606/45 |
| 2938259 | 4/1981 | Germany | 606/47 |
| 3347122 | 6/1985 | Germany | 606/47 |

OTHER PUBLICATIONS

Waye, J.D. et al. "The Lost Polyp: A Guide to Retrieval During Colonoscopy" Int. J. Colorect. Dis. (1988) 3:229–231.

Ricca, J.J. "Retrieval of Polyps Severed at Colonoscopy" Gastrointestinal Endoscopy (1977) 24, 1:44.

Maas, L.C. et al. "Polyp Retrieval Impossible Without Colonoscope Tip" and Ward, W.J. Reply Gastrointestinal Endoscopy (1984)30, 6:378.

Abrams, J.S. "A Hard Look at Colonoscopy" The American Journal of Surgery (Jan. 1977) 133:111–115.

Schwesinger, W.H. "Complications in Colonoscopy" Surgery, Gynecology & Obstetrics (Feb. 1979) 148:270–281.

(List continued on next page.)

*Primary Examiner*—Robert A. Hafer
*Assistant Examiner*—Justine R. Yu
*Attorney, Agent, or Firm*—R. Neil Sudol; Henry D. Coleman

[57] ABSTRACT

A method for removing a polyp from a patient utilizes (i) a flexible conductive cauterization loop and (ii) a flexible auxiliary loop to which a flexible web member is connected to define an expandable pocket, the cauterization loop and the auxiliary loop being disposed in a common tubular member. Upon insertion of an endoscope assembly into a patient and a locating of the polyp, the tubular member is moved through the biopsy channel of the endoscope to eject a distal end portion of the tubular member from the biopsy channel. The cauterization loop is then shifted in a distal direction relative to the ejected tubular member to eject the cauterization loop from the tubular member. The cauterization loop is manipulated from outside of the patient to pass the loop over the polyp and to at least partially close the loop to engage the polyp around a base region thereof. Upon a subsequent conducting of an electrical current through the cauterization loop to burn through the polyp at the base region, thereby severing the polyp at the base region, the cauterization loop is retracted into the tubular member and the auxiliary loop is ejected and maneuvered to enclose the severed polyp in the capture pocket. The auxiliary loop is at least partially closed to capture the severed internal body tissues in the pocket. The captured polyp is removed in the pocket from the patient.

7 Claims, 20 Drawing Sheets

U.S. PATENT DOCUMENTS

| | | | |
|---|---|---|---|
| 1,609,014 | 11/1926 | Dowd | 606/114 |
| 3,472,230 | 10/1969 | Fogarty | 606/127 |
| 3,715,829 | 2/1973 | Hamilton | 43/12 |
| 4,202,338 | 5/1980 | Bitrolf | 606/47 |
| 4,326,530 | 4/1982 | Fleury, Jr. | 606/47 |
| 4,345,599 | 8/1982 | McCarrell | 606/113 |
| 4,493,320 | 1/1985 | Treat | 606/47 |
| 4,503,855 | 3/1985 | Maslanka | 606/47 |
| 4,516,347 | 5/1985 | Dickie | 43/11 |
| 4,557,255 | 12/1985 | Goodman | 606/127 |
| 4,638,802 | 1/1987 | Okada | 606/47 |
| 4,643,187 | 2/1987 | Okada | 606/47 |
| 4,705,041 | 11/1987 | Kim | 606/108 |
| 4,718,419 | 1/1988 | Okada | 128/4 |
| 4,800,870 | 1/1989 | Reid, Jr. | |
| 4,997,435 | 3/1991 | Demeter | 606/127 |
| 5,037,379 | 8/1991 | Clayman et al. | |
| 5,084,054 | 1/1992 | Bencini et al. | 606/127 |
| 5,122,147 | 6/1992 | Sewell | 606/113 |
| 5,143,082 | 9/1992 | Kindberg et al. | |
| 5,147,371 | 9/1992 | Washington et al. | |
| 5,158,561 | 10/1992 | Rydell et al. | |
| 5,190,542 | 3/1993 | Nakao et al. | 606/113 |
| 5,195,954 | 3/1993 | Schnepp-Pesch et al. | 606/127 |
| 5,201,740 | 4/1993 | Nakao et al. | 606/113 |
| 5,201,741 | 4/1993 | Dulebohn | 606/113 |
| 5,279,539 | 1/1994 | Bohan et al. | 606/113 |
| 5,312,416 | 5/1994 | Spaeth et al. | 606/114 |
| 5,341,815 | 8/1994 | Cofone et al. | 600/37 |
| 5,352,184 | 10/1994 | Goldberg et al. | 606/127 |
| 5,354,303 | 10/1994 | Spaeth et al. | 606/113 |
| 5,366,460 | 11/1994 | Eberbach | 606/1 |
| 5,368,597 | 11/1994 | Pagedas | 606/114 |
| 5,417,697 | 5/1995 | Wilk et al. | 606/113 |

OTHER PUBLICATIONS

Sugarbaker, P.H. "Colonoscopy in the Management of Diseases of the Colon and Rectum" Surgery, Gynecology & Obstetrics (Sep. 1974) 139:341–349.

Kobayashi, S. "Colonoscopic Polypectomy with Special Reference to Management of Multiple Polyps" (Kitano H. et al.) Gastro. Endosc. (1983)29, 4:335–6.

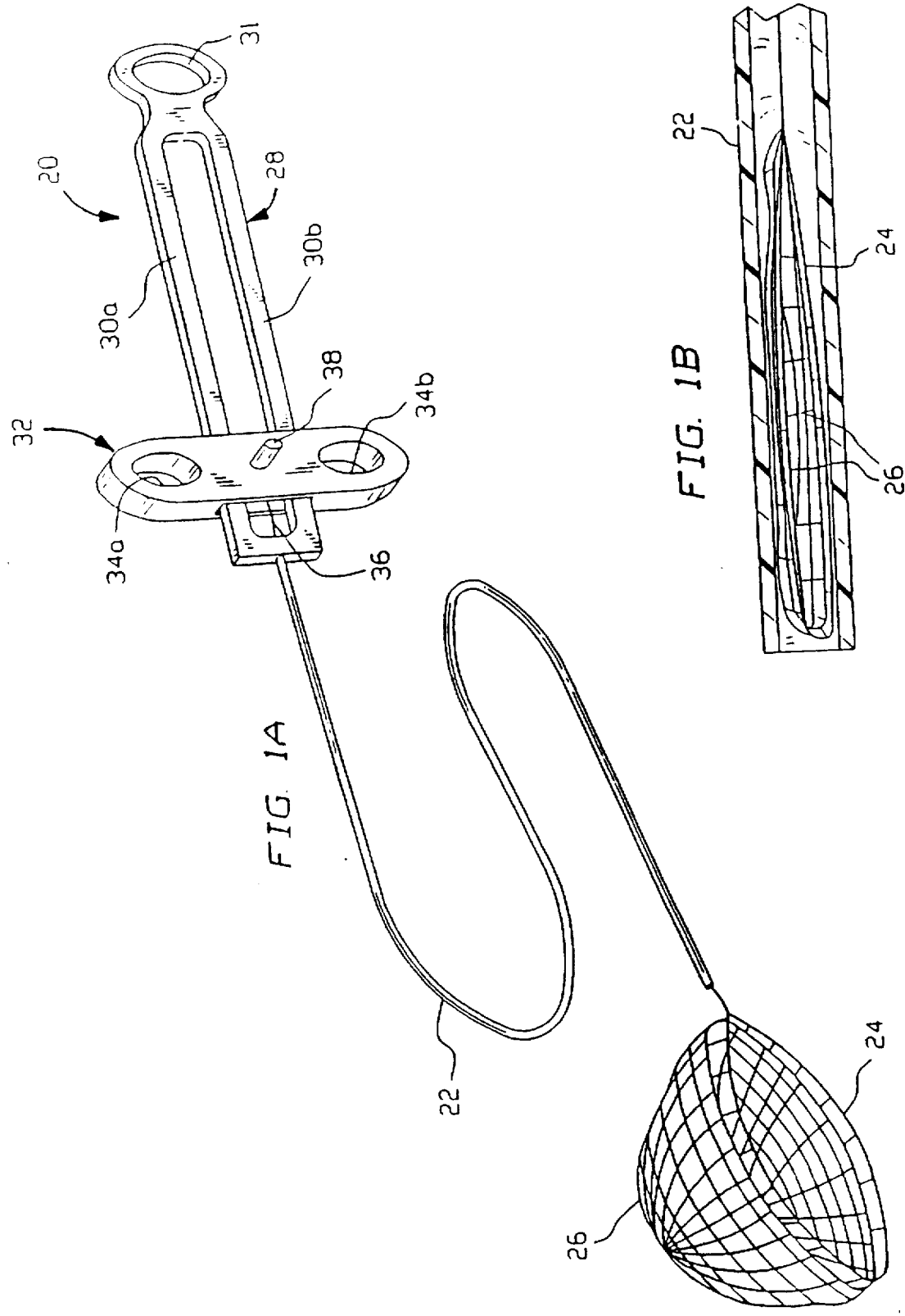

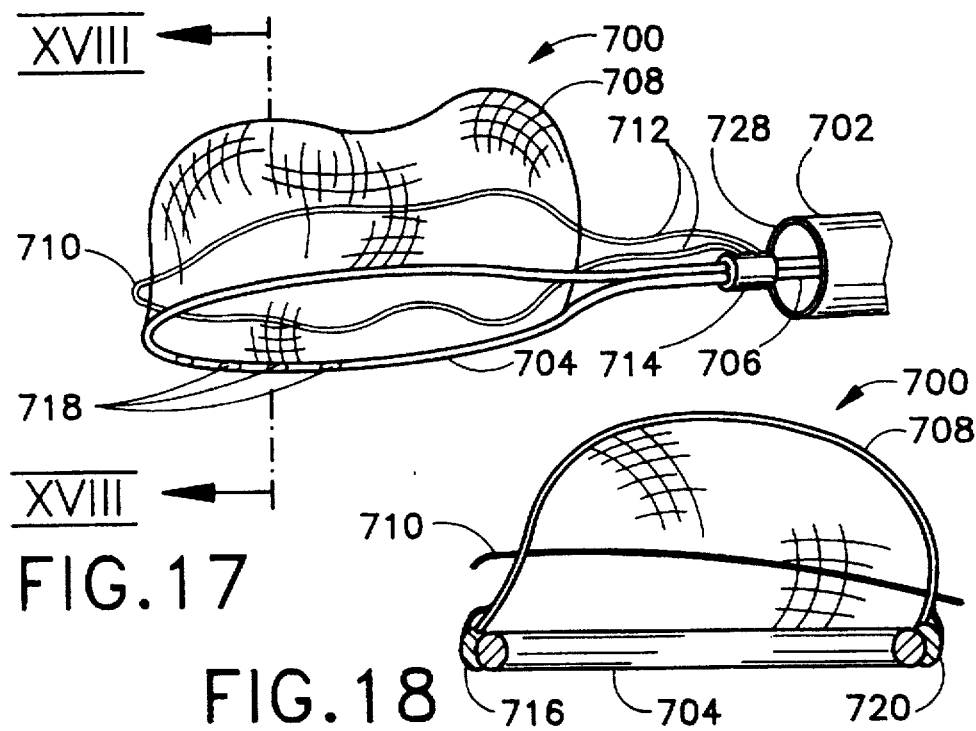
FIG.17
FIG.18
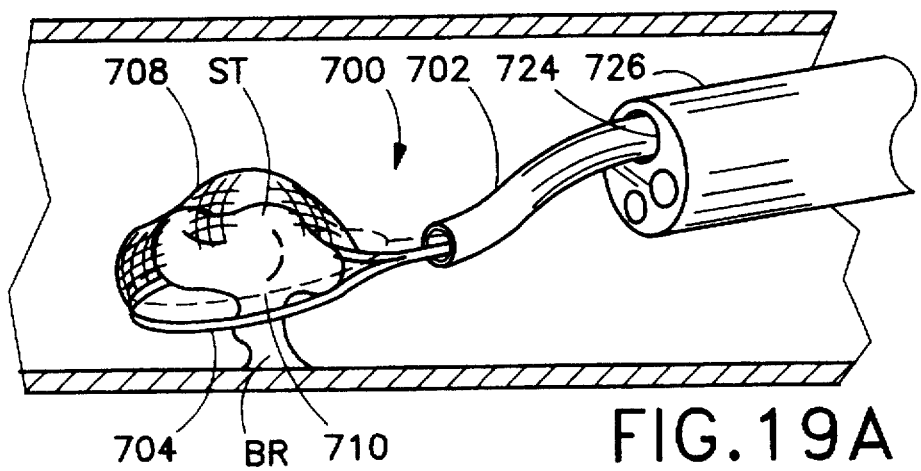
FIG.19A
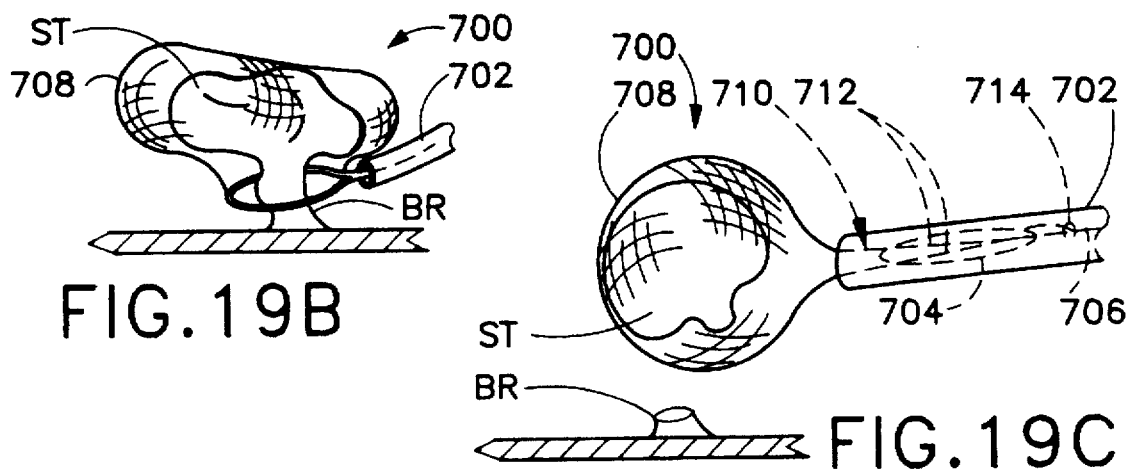
FIG.19B
FIG.19C

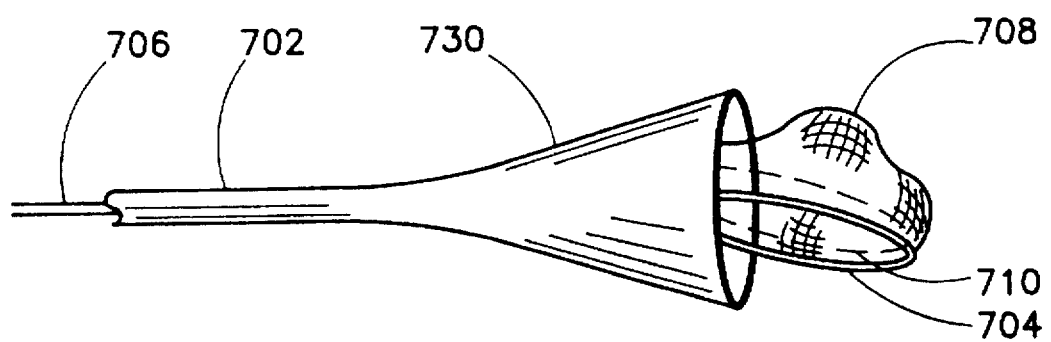
FIG. 20A
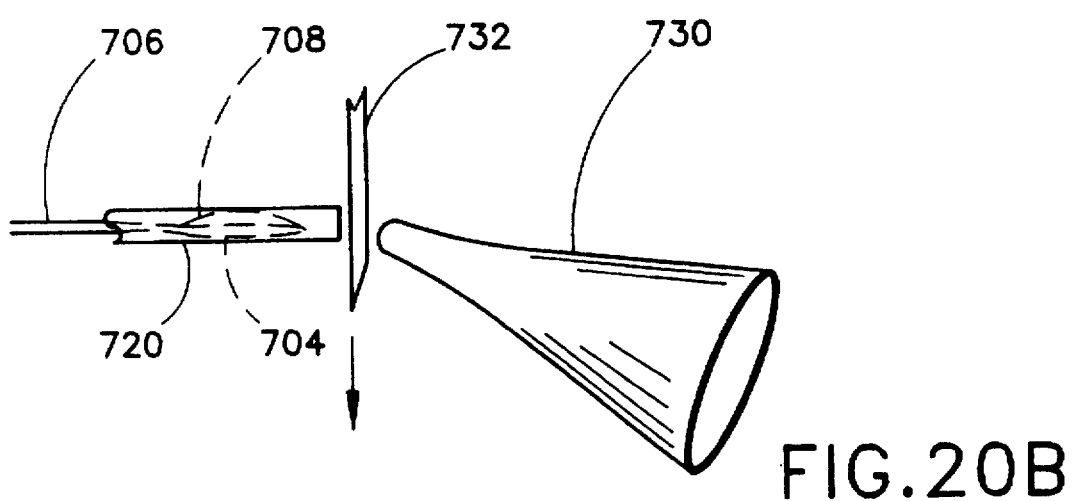
FIG. 20B
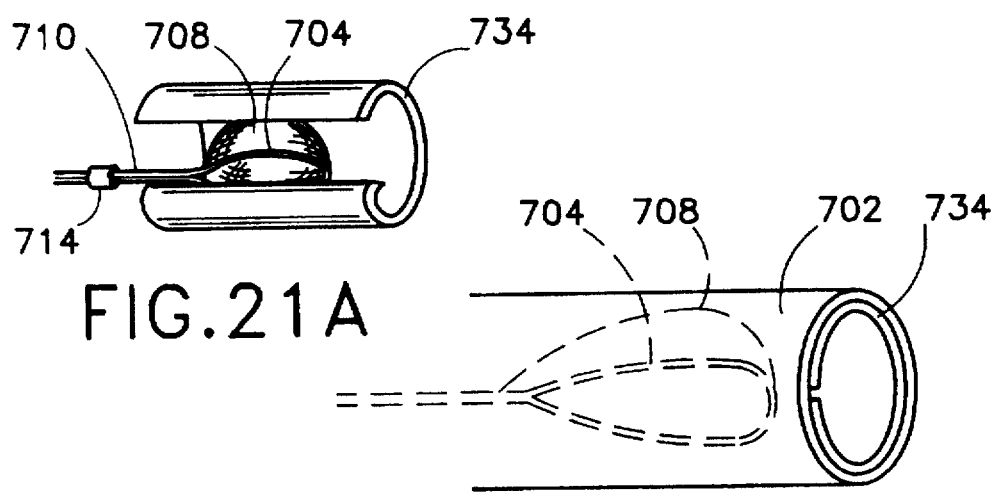
FIG. 21A
FIG. 21B

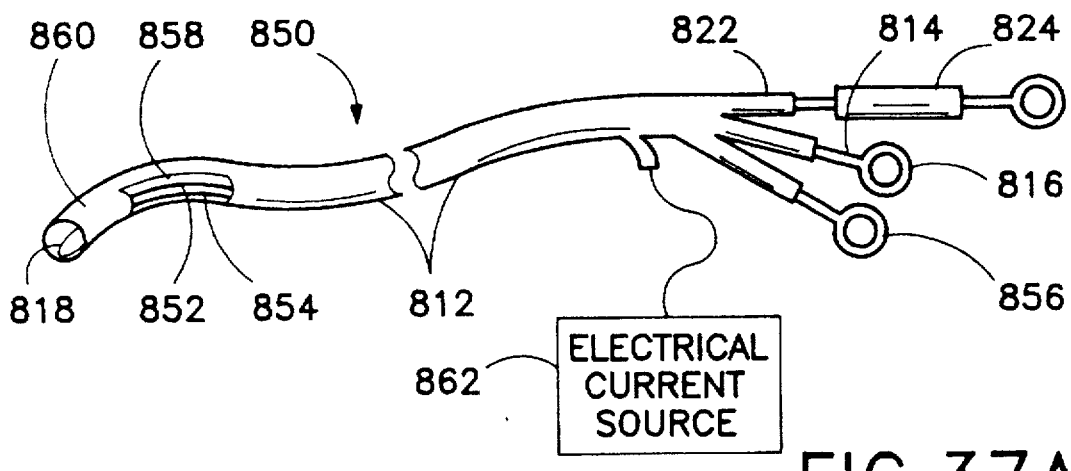
FIG.37A
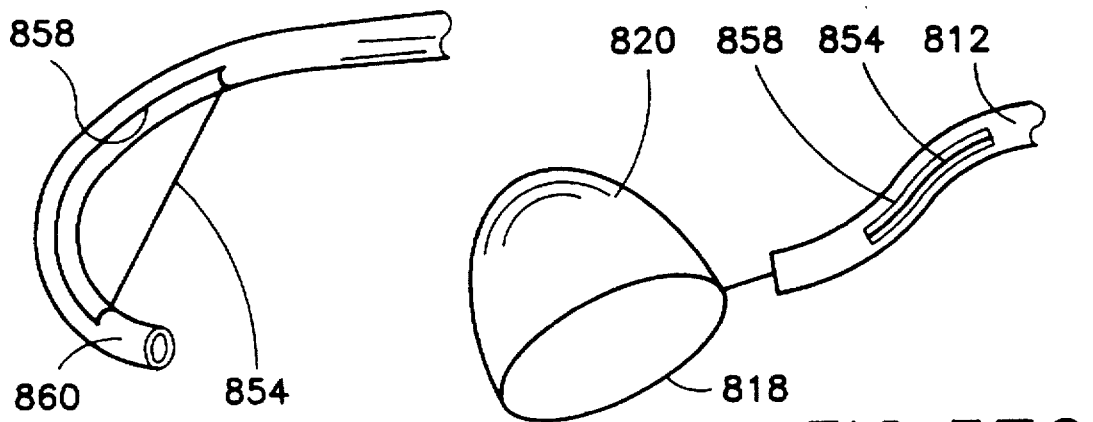
FIG.37B
FIG.37C
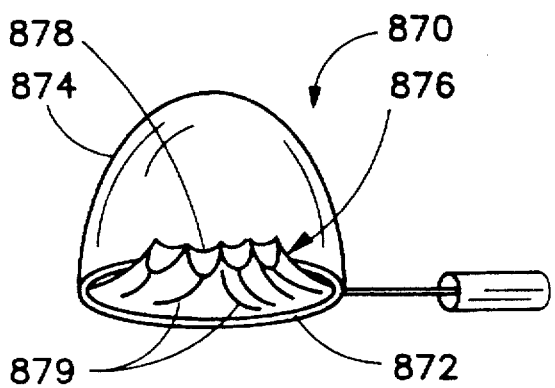
FIG.38
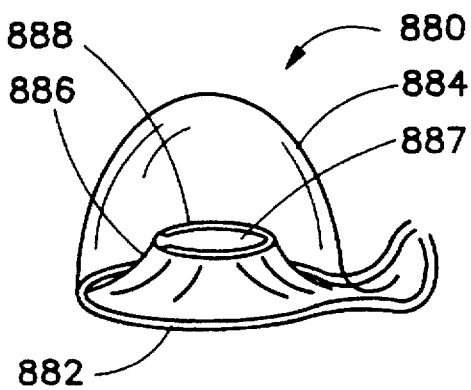
FIG.39

SURGICAL RETRIEVAL ASSEMBLY AND ASSOCIATED METHOD

CROSS REFERENCE TO RELATED APPLICATIONS

This application is a continuation-in-part of commonly owned application Ser. No. 08/213,196 filed Mar. 14, 1994, now U.S. Pat. No. 5,486,185 as a continuation-in-part of commonly owned application Ser. No. 08/012,657 in turn filed Feb. 1, 1993, now U.S. Pat. No. 5,336,227 as a continuation-inpart of commonly owned application Ser. No. 07/788,035 filed Nov. 5, 1991, now U.S. Patent No. 5,201,740, and a continuation-in-part of commonly owned application Ser. No. 07/892,214 filed Jun. 2, 1992, now U.S. Pat. No. 5,190,542. This application is also a continuation-in-part of commonly owned application Ser. No. 07/957,416 filed Oct. 5, 1992, now U.S. Pat. No. 5,374,273.

FIELD OF THE INVENTION

This invention relates to a surgical instrument assembly for use in retrieving objects from internal body cavities. This invention also relates, more specifically, to a surgical instrument assembly for use in snare cauterization operations. This invention thus relates to an associated method for severing internal organic tissues and retrieving the severed tissues and more particularly to a method for removing or retrieving polyps and other clumps of organic tissue.

BACKGROUND OF THE INVENTION

In a conventional endoscopic snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In some cases, the endoscope must be removed without the polyp and the patient given an enema in an attempt to flush out the polyp from the colon.

Furthermore, there are numerous cases where a severed polyp is never recovered. Sometimes, the polyp is masticated during the retrieval attempt. In all such cases, the pathologist is unable to determine whether the polyp contains carcinoma in situ (localized) or infiltrative carcinoma (spread). The patient must then undergo a colon ressection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

U.S. Pat. No. 5,201,740 of Nakao et al. provides a solution to the above-described problems in polyp removal. Pursuant to the disclosure of that patent, snare cauterization operations are performed with a surgical instrument assembly comprising a tubular sheath member carrying a metallic cauterization loop and a metal wire operatively connected to the loop, the wire passing longitudinally through the sheath. An electrical supply is operatively connectable to the wire, while a flexible web member is connected to the loop to form a capture pocket, the loop defining a mouth opening of the pocket. During use of the snare cauterization loop, the web member is passed over and substantially surrounds a polyp. The pocket captures the polyp at the same time that the cauterization loop is energized to effectuate a severing of the polyp.

This cauterization snare assembly with attached pocket is a substantial advance over conventional polyp removal techniques. However, in some cases, the pocket can obscure the polyp from visualization via the endoscope's optical system, making it difficult to obtain an optimal severing of the polyp. For example, if a polyp is located behind a fold of colonic tissues, it can be difficult to manipulate a cauterization snare to place it around the polyp. If a pouch is attached to the cauterization loop, the pouch may inhibit effective visualization of the polyp, thereby increasing the difficulty of the cauterization snare procedure.

An affliction similar to polyps because of a related method of treatment is gall stones, i.e., small stones formed from natural biological processes from chemical substances in the bile. These stones sit in the gall bladder and are frequently removed during a cholecystectomy. In a cholecystectomy, the cystic duct is clamped and severed and the gall bladder is removed, thereby removing any stones in the bladder. However, some stones are frequently retained in the common bile duct.

Currently, the stones in the common bile duct are retrieved using a Dormia basket. That instrument includes a series of wires of spring biased construction which are connected to form an ovoidal or football shaped cage upon the release of the basket from the distal end of a tubular member.

The distal end of the tubular member is inserted through the Ampulla of Vater at one end of the common bile duct or, alternatively, through a bile duct over the liver. The Dormia basket may also be inserted through a tubular prosthesis or bridge extending from the abdominal wall to the wall of the common bile duct where the bridging member is inserted into the duct.

A Dormia basket is difficult to manipulate in order to capture retained common bile duct stones. Such operations can take hours for an essentially simple task. The task is made even more difficult and time consuming if several stones are to be retrieved from the duct.

Commonly owned U.S. patent application Ser. No. 07/957,416 filed Oct. 5, 1992 provides a solution to the above-discussed problems in the removal of bile duct stones. In accordance with that solution, a distal end of a flexible tubular member is introduced into the common bile duct via the Ampulla of Vater. The tubular member carries a loop to which a flexible web is attached to form a capture pocket and is also provided with a separate cauterization wire. The wire protrudes through a window in the tubular member upon a bending of the distal end thereof and is used as a cutting tool to increase the opening of the Ampulla of Vater. Subsequently, the distal end portion of the tubular member is inserted through the enlarged opening into the common bile duct. The loop and pocket are then ejected from the distal end of the tubular member and moved through the common bile duct to capture a retained stone in the pocket. Subsequently, the loop and the pocket are at least partially closed by drawing the loop and the pocket in a proximal direction into the distal end of the tubular member, thereby enclosing the captured stone in the pocket. The tubular member and the contracted loop and pocket are withdrawn from the common bile duct, thereby removing the captured stone from the common bile duct.

OBJECTS OF THE INVENTION

An object of the present invention is to provide an improved method for the removal of polyps and other organic tissue parts from patients.

A more specific object of the present invention is to provide an improved method for the performance of a snare cauterization operation.

A related object of the present invention is to provide a snare cauterization technique wherein the capture and retrieval of severed polyps is facilitated.

A further object of the present invention is to provide an instrument assembly for use in removing polyps and other tissue clumps from patients.

Another particular object of the present invention is to provide such an instrument assembly which is simple to manufacture and therefore inexpensive.

A further particular object of the present invention is to provide such an instrument assembly which is easy to use.

Yet another object of the present invention is to provide a snare cauterization instrument assembly wherein a polyp is severed and subsequently captured before it has had an opportunity to roll away.

These and other objects will be apparent from the following descriptions.

SUMMARY OF THE INVENTION

A method for removing a selected portion of internal body tissues of a patient utilizes, in accordance with the present invention, (i) a flexible conductive cauterization loop and (ii) a flexible auxiliary loop to which a flexible web member is connected to define an expandable pocket, the cauterization loop and the auxiliary loop being disposed in a common tubular member. A handle assembly is operatively connected to the cauterization loop and the auxiliary loop so as to allow those two elements to be ejected independently from the common tubular member or catheter.

The method includes the steps of (a) inserting an endoscope assembly into a patient, (b) using the endoscope assembly to visually monitor internal body tissues of the patient upon insertion of the endoscope assembly into the patient, (c) moving the tubular member in a distal direction through the biopsy channel to eject a distal end portion of the tubular member from the biopsy channel upon detecting selected internal body tissues to be removed from the patient, (d) shifting the cauterization loop in a distal direction relative to the tubular member to eject the cauterization loop from the tubular member upon ejection of the distal end portion of the tubular member from the biopsy channel, (e) at least partially expanding the cauterization loop from a collapsed configuration upon ejection of the cauterization loop from the tubular member, and (f) manipulating the expanded cauterization loop from outside of the patient to pass the expanded cauterization loop over the selected internal body tissues to be removed. Further steps include (g) ejecting the auxiliary loop from the tubular member upon a passing of the expanded cauterization loop over the selected internal body tissues to be removed, (h) at least partially opening the auxiliary loop from a folded configuration upon ejection of the auxiliary loop from the tubular member, and (i) maneuvering the opened auxiliary loop from outside of the patient to pass the opened auxiliary loop over the selected internal body tissues so that the web member substantially surrounds the selected internal body tissues. Additional steps include (j) at least partially closing the cauterization loop to engage the selected internal body tissues around a base region thereof upon a passing of the expanded cauterization loop over the selected internal body tissues to be removed, (k) conducting an electrical current through the closed cauterization loop to burn through the selected internal body tissues at the base region, thereby severing the selected internal body tissues at the base region, (l) retracting the cauterization loop into the tubular member upon the severing of the selected internal body tissues at the base region, and (m) at least partially closing the auxiliary loop to capture the severed internal body tissues in the pocket.

According to another feature of the present invention, the auxiliary loop is ejected from the tubular member and maneuvered over the selected internal body tissues prior to the conducting of electrical current in the cauterization cutting operation. In addition, the auxiliary loop is closed substantially simultaneously with the closing of the cauterization loop.

According to an alternative feature of the present invention, the auxiliary loop from the tubular member is executed only upon completion of the step of retracting the cauterization loop into the tubular member, the auxiliary loop being maneuvered over the selected internal body tissues only upon severing of the selected internal body tissues by the cauterization loop.

The cauterization loop is closed by shifting the tubular member and the cauterization loop relatively towards one another to thereby at least partially withdraw or retract the cauterization loop into the tubular member. Similarly, the closing of the auxiliary loop includes shifting the tubular member and the auxiliary loop relative to one another to thereby at least partially withdraw the auxiliary loop into the tubular member.

According to a further feature of the present invention, the tubular member is provided with means for defining a pair of longitudinally extending lumens. The cauterization loop is thus slid or shifted through or along one of the lumens, while the auxiliary loop is ejected from the tubular member upon a sliding of the auxiliary loop through or along another lumen of the tubular member.

The method contemplates that the captured internal body tissues are removed from the patient together with the auxiliary loop and the capture pocket.

A surgical instrument assembly for use in snare cauterization operations comprises, in accordance with the present invention, a tubular member defining a plurality of separate longitudinally extending lumens, the tubular member having a diameter sufficiently small so that the tubular member can be inserted through a biopsy channel of a flexible endoscope. The instrument assembly further comprises a cauterization loop and an auxiliary loop. An electrically conductive wire is operatively connected to the cauterization loop, the cauterization loop and the wire being disposed at least partially in one of the lumens of the tubular member. An electrical supply or coupling is operatively connected to the wire for feeding an electrical current to the cauterization loop via the wire. An elongate flexible shifting member (e.g., a wire) is connected at one end to the auxiliary loop, the auxiliary loop and the shifting member being at least partially disposed in another lumen of the tubular member. A flexible web member is connected to the auxiliary loop so as to form a capture pocket, the auxiliary loop defining a mouth opening of the pocket.

In accordance with another feature of the present invention, the instrument assembly further comprises at least one flexible tensile member connected to the flexible web member at a proximal end thereof and to the tubular member at a point spaced from a distal end thereof, the tensile member extending from the flexible web member into the lumen of the tubular member traversed by the elongate shifting member of the auxiliary loop.

In accordance with a more specific feature of the present invention, the flexible tensile member is one of a plurality of flexible tensile member segments each connected to the flexible web member at the proximal end thereof and to the tubular member, the tensile member segments each extending from the flexible web member into another of the lumens. Even more specifically, the tensile member segments are parts of a single flexible tensile member which extends through a pair of holes in the tubular member. A patch may be disposed on an outer surface of the tubular member over the holes.

The web member, whether a net or a continuous film of polymeric material, may be slidably connected to the auxiliary loop at a plurality of spaced locations, e.g., via ringlets.

The tubular member is preferably flexible so that it may pass along bends in an endoscope insertion member upon a deployment thereof during an endoscopic investigation.

Pursuant to another conceptualization of the present invention, a surgical instrument assembly comprises, in accordance with the present invention, a tubular member defining at least one longitudinally extending lumen, the tubular member having a diameter sufficiently small so that the tubular member can be inserted through a biopsy channel of a flexible endoscope. An elongate flexible shifting member is connected at one end to a flexible loop, the loop and the shifting member being at least partially disposed in the lumen of the tubular member. A flexible web member is connected to the loop so as to form a capture pocket. The loop defines a mouth opening of the pocket. At least one flexible tensile member is connected to the flexible web member at a proximal end thereof and to the tubular member at a point spaced from a distal end thereof. The tensile member extends from the flexible web member into the lumen of the tubular member.

According to yet another conceptualization of the present invention, an endoscopic surgical instrument for use in snare cauterization operations comprises a tubular sheath member, an alternately expandable and contractible cauterization loop, an electrically conductive wire operatively connected to the loop, the wire being slidable longitudinally through the sheath, and a flexible web member connected to the loop essentially around a circumference thereof to form a capture pocket. The loop defines a mouth opening of the pocket. The web member is slidably attached to the loop along a proximal portion thereof and is fixed to the loop along a distal portion thereof in such a manner as to be separable from the loop so as to enable at least a substantial separation of the web member from the loop upon a proximally directed cutting or cauterizing stroke of the wire at the termination of a cauterization operation.

According to another feature of the present invention, this endoscopic surgical instrument further comprises a purse string attached to the web member along a ring shaped locus proximately to the mouth opening. Preferably, the purse string is attached at a proximal end to at least one of the wire and the tubular member.

According to another feature of the present invention, the web member is attached, e.g., via adhesive, to a radially outwardly facing surface area of the loop along the distal portion thereof. Alternatively, the web member is attached at a plurality of discrete points to the loop along the distal portion thereof. Such an attachment may be implemented by inserting tiny rings or threads of the web member around the loop or through individual metal filaments of the loop.

The present invention provides an improved method for the removal of polyps and other internal organic parts from patients via snare cauterization. A snare and a capture pocket are introducible separately into a hollow internal organ, thereby facilitating placement of the cauterization snare.

In a method in accordance with the present invention, the capture and retrieval of severed polyps is facilitated. An instrument assembly in accordance with the present invention is simple to use. Accordingly, trauma to the patient and time in surgery are reduced. More specifically, time under anaesthesia with the accompanying side effects is reduced. Concomitantly, the expense of hospitalization is decreased.

An instrument assembly in accordance with the present invention allows one to perform a conventional polyp severing operation and then to subsequently capture the severed polyp before it has a chance to roll away. The capture pocket may be placed about the polyp after the cauterization loop is in place and before cutting occurs. Alternatively, the capture pocket or pouch may be ejected from the common tubular instrument guide only after the cauterization operation is completed. In either case, the capture pocket remains out of the way until the cauterization loop is placed over the polyp and is in place for the cauterization operation.

BRIEF DESCRIPTION OF THE DRAWING

FIG. 1A is a schematic perspective view of a snare cauterization instrument assembly, showing a cauterization loop in an ejected, use configuration.

FIG. 1B is a schematic longitudinal cross-sectional view of a distal end of the cauterization instrument assembly of FIG. 1A, showing the cauterization loop in a withdrawn or retracted storage configuration inside the distal end of a tubular member of the instrument assembly.

FIG. 17 is a schematic side elevational view, on an enlarged scale, of a cauterization snare assembly.

FIG. 18 is a schematic cross-sectional view, on an enlarged scale, taken along line XVIII–XVIII in FIG. 17.

FIGS. 19A–19C are schematic side elevational views of the cauterization snare assembly of FIGS. 17 and 18, showing successive steps in the use of the assembly of FIGS. 17 and 18.

FIGS. 20A and 20B are schematic side elevational views of a snare assembly, showing successive steps in a manufacturing process.

FIGS. 21A and 21B are schematic perspective views of a snare assembly, showing successive steps in another manufacturing process.

FIG. 37A is a schematic perspective view of another modified snare device.

FIG. 37B is a partial perspective view of the modified snare device of FIG. 37A, depicting an operational configuration of that device.

FIG. 37C is a partial perspective view of the modified snare device of FIG. 37A, depicting another operational configuration of that device.

FIG. 38 is a schematic perspective view of yet another modified snare device.

FIG. 39 is a schematic perspective view of an additional modified snare device.

The same elements and organs in the different figures bear the same reference designations.

DETAILED DESCRIPTION

Figure 2A:
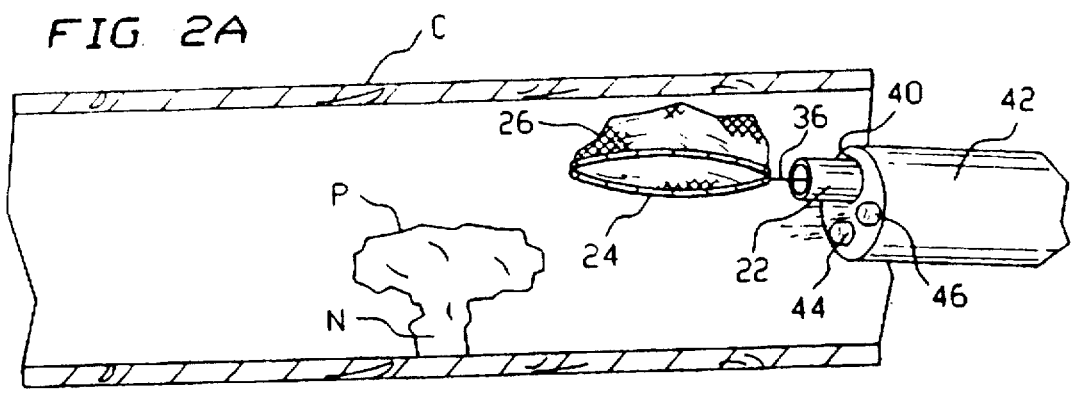
FIG. 2A is a schematic partial cross sectional view of a patient's colon with a polyp, showing the snare cauterization instrument assembly of FIG. 1A inserted in the biopsy channel of an endoscope which is itself inserted into the patient's colon, and further showing the instrument assembly in an initial stage of a snare cauterization procedure.

As illustrated in FIG. 1A, a snare cauterization instrument assembly comprises a hand held control module 20, a flexible tubular member 22 connected to a distal end of the control module, and an alternately expandable and closable cauterization loop 24 at the distal tip of the flexible tubular member 22. A flexible sheet or web 26 specifically in the form of a net is attached to cauterization loop 24 for defining a capture pocket. Loop 24 defines the mouth of the capture pocket.

Control module 20 comprises a body member or frame 28 which includes a pair of parallel rails 30a and 30b to which a slider member 32 is reciprocatably secured. Frame 28 has a thumb hole 31 at a proximal end, whereas slider member 32 has a pair of finger holes 34a and 34b and is fastened to the proximal end of a wire 36 which passes through tubular member 22 and is in turn connected to cauterization loop 24 at the distal end of tubular member 22. Wire 36 is sufficiently flexible to bend with tubular member 22 during the negotiation thereby of curves or bends in a colon during surgery.

Slider member 32 is also provided with an electrical connector 38 which is couplable to a source of electrical energy. During a severing step of a cauterization operation, described in detail hereinafter with reference to FIG. 2E, electrical energy is fed to loop 24 via connector 38 and wire 36.

Capture web 26 is thin and flexible and preferably made of biologically inert flexible transparent synthetic resin or polymeric material such as polyethylene or nylon. Prior to the beginning of a snare cauterization operation, web 26 is disposed in a closed, folded or contracted state, together with loop 24, in the distal end of tubular member 22, as illustrated in FIG. 1B. Concomitantly, slider member 32 is retracted to the proximal end of rails 30a and 30b (towards the right side of frame 28 in FIG. 1A). Tubular member 22 is inserted in a biopsy channel 40 of an endoscope 42, as shown in FIG. 2A, and the endoscope is inserted into a body cavity of a patient, such as a colon C.

As illustrated further in FIG. 2A, endoscope 42 is conventionally provided at its distal end with a pair of apertures 44 and 46 for respectively delivering light to and receiving light from a surgical site.

Upon the discovery of a polyp P within colon C via the use of endoscope 42, the snare cauterization instrument assembly is shifted in a distal direction so that tubular member 22 protrudes from the distal end of biopsy channel 40. Then, slider member 32 is shifted in a distal direction to eject loop 24 and capture web 26 from tubular member 22. Upon ejection, loop 24 and capture web 26 expand from a contracted or closed configuration into an at least partially opened configuration, as shown in FIG. 2A.

Figure 2B:
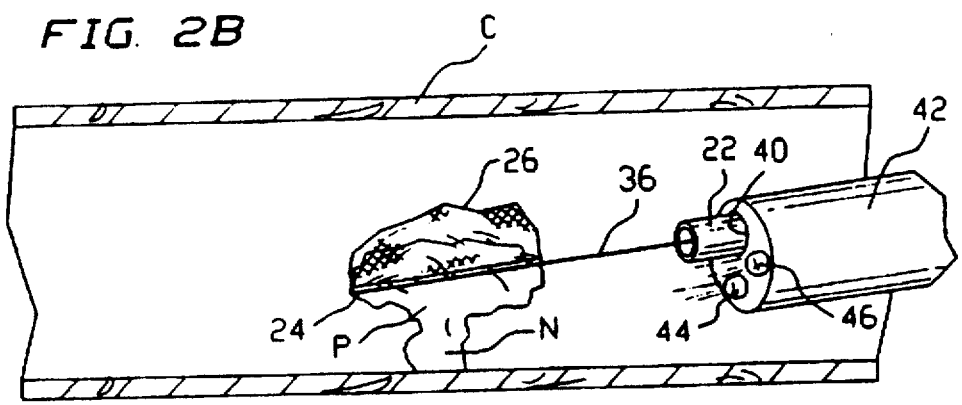
FIG. 2B is a schematic partial cross sectional view similar to FIG. 2A, showing a loop of the snare cauterization instrument assembly of FIG. 1A being passed around the polyp of FIG. 2A.
Figure 2C:
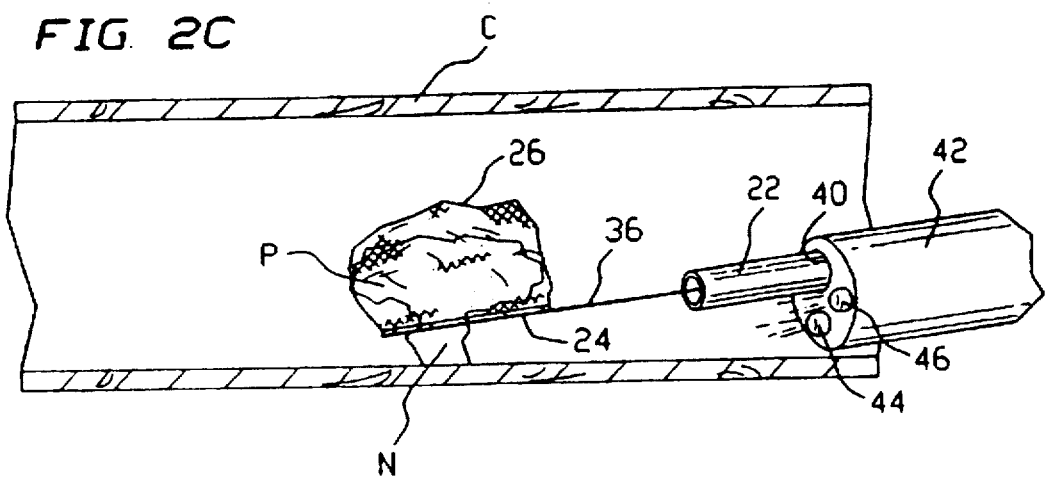
FIG. 2C is a schematic partial cross sectional view similar to FIGS. 2A-2B, showing the loop of the snare cauterization instrument assembly of FIG. 1A completely passed around the polyp of FIG. 2A.

FIG. 2B depicts a later stage in the cauterization procedure. The snare cauterization instrument assembly of FIG. 1A is manipulated to pass loop 24 around polyp P, with capture web 26 following. Eventually, loop 24 encircles a base region or neck N of polyp P and the polyp is surrounded by capture web 26, as shown in FIG. 2C.

Figure 2D:
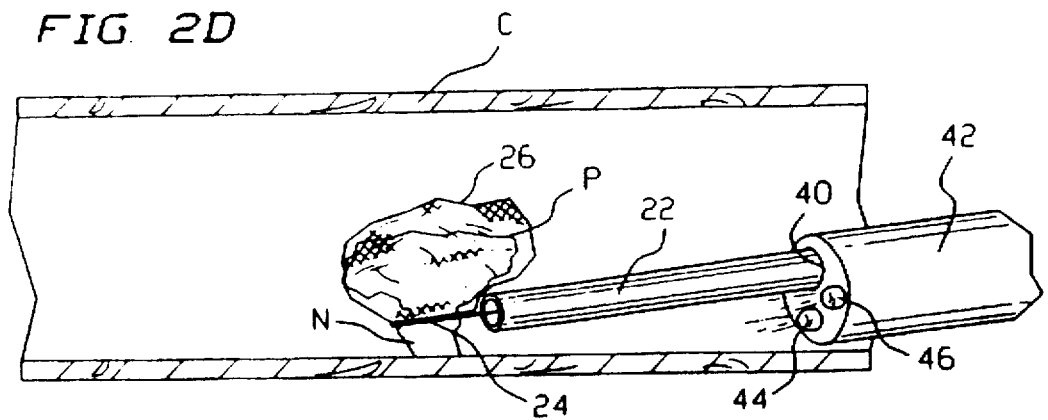
FIG. 2D is a schematic partial cross sectional view similar to FIGS. 2A-2C, showing the loop of the snare cauterization instrument assembly of FIG. 1A being tightened around a base or neck of the polyp.

At that juncture, slider member 32 is pulled back in the proximal direction, whereby wire 36 pulls loop 24 partially back into the distal end of tubular member 22, thereby causing loop 24 to tighten about neck N of polyp P, as illustrated in FIG. 2D.

Figure 2E:
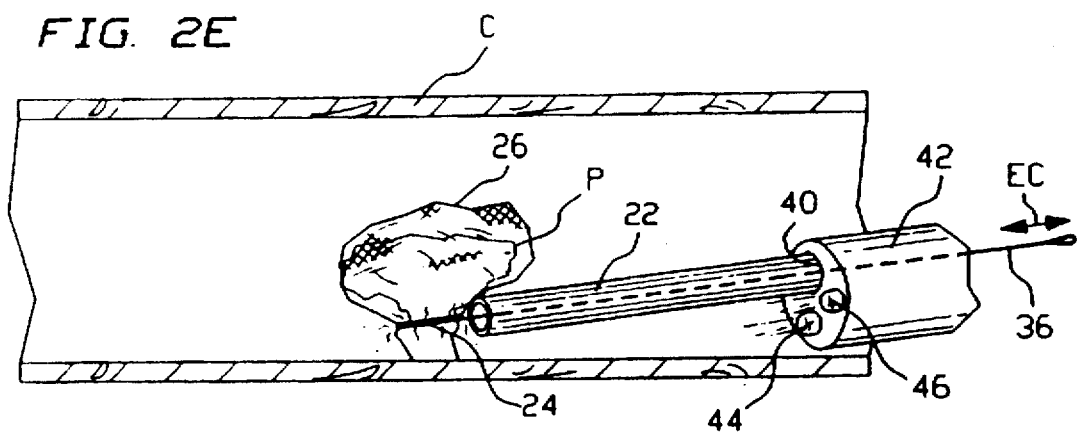
FIG. 2E is a schematic partial cross sectional view similar to FIGS. 2A-2D, showing the loop of the snare cauterization instrument assembly of FIG. 1A in an electrically energized state for burning through the base or neck of the polyp.
Figure 2F:
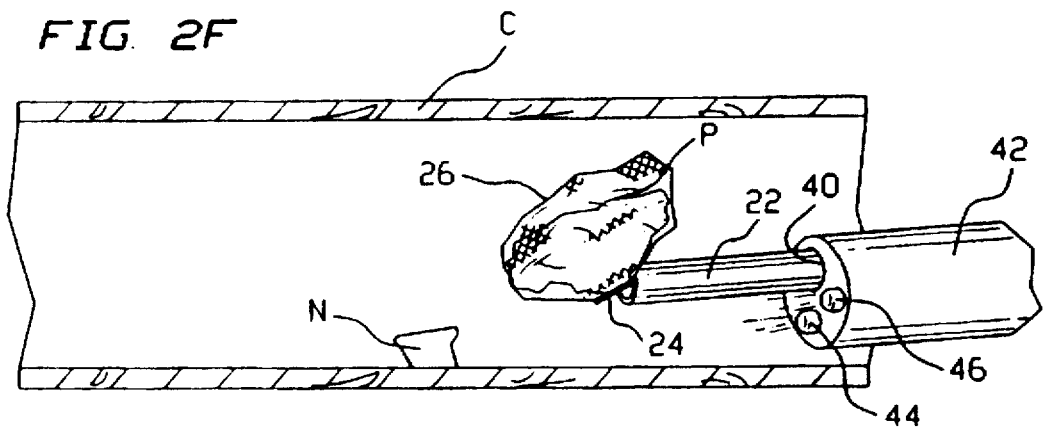
FIG. 2F is a schematic partial cross sectional view similar to FIGS. 2A-2E, showing the polyp severed from the colon wall and captured with the snare cauterization instrument assembly of FIG. 1A.
Figure 2G:
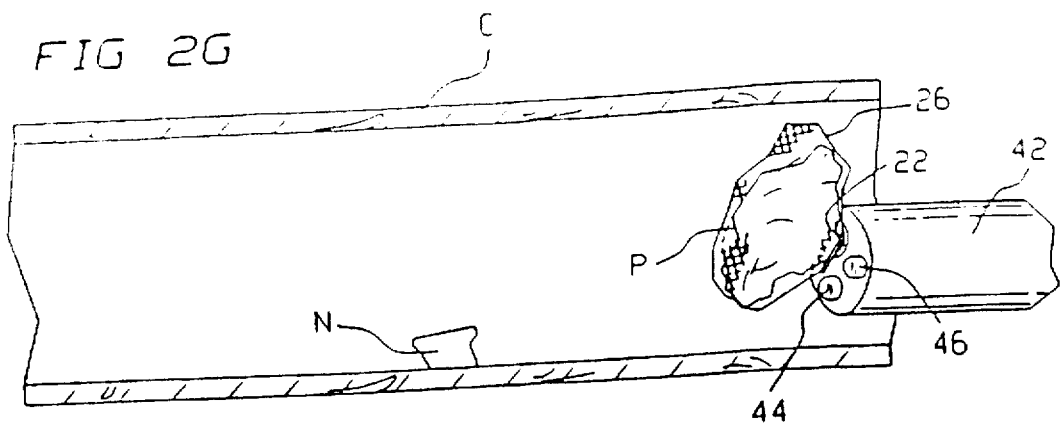
FIG. 2G is a schematic partial cross sectional view similar to FIGS. 2A-2F, showing the snare cauterization instrument assembly of FIG. 1A together with the captured polyp drawn towards the distal end of the endoscope.

As indicated in FIG. 2E, electrical current EC is then caused to pass through wire 36 and loop 24. Generally, electric current from loop 24 is conducted through neck N of polyp P, thereby generating in the polyp tissues heat sufficiently great to sever and cauterize neck N. Upon the severing of polyp P at neck N, slider member 32 is pulled farther in the proximal direction, thereby pulling loop 24 further into the distal end of tubular member 22, as shown in FIG. 2F, to essentially close the loop. Polyp P is now securely trapped in capture web 26. In a further step, depicted in FIG. 2G, the entire snare cauterization instrument assembly including, in particular, tubular member 22, is shifted in the proximal direction relative to endoscope 42. However, care is taken not to draw the distal end of tubular member 22 and particularly capture web 26 with polyp P back into biopsy channel 40 of the endoscope. Polyp P remains in web or capture pocket 26 outside of tubular member 22 and endoscope 42 during the withdrawal of endoscope 42 from the patient.

Every polyp severed by a snare cauterization instrument as described and illustrated herein is captured immediately. Thus, the time for the capture and retrieval of severed polyps is reduced to a minimum. Trauma to patient is likewise reduced, as are hospitalization expenses.

Figure 3:
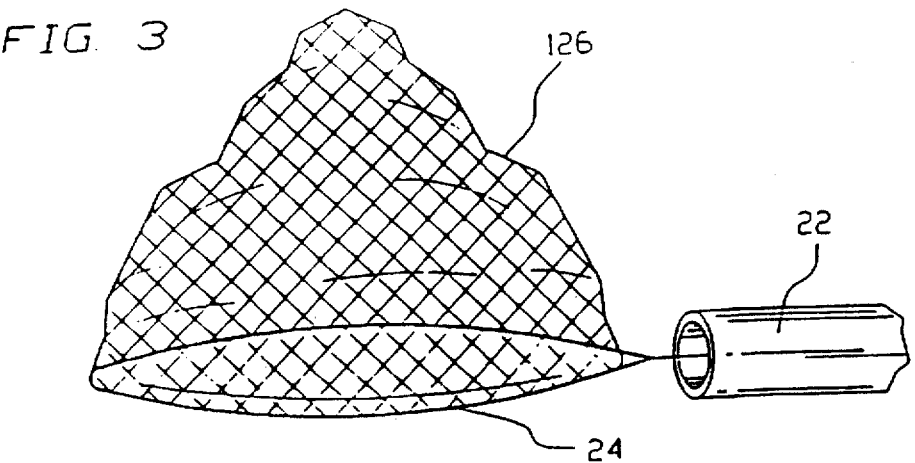
FIGS. 3–6 are schematic partial side perspective views, showing different specific embodiments of a snare cauterization instrument assembly.
Figure 4:
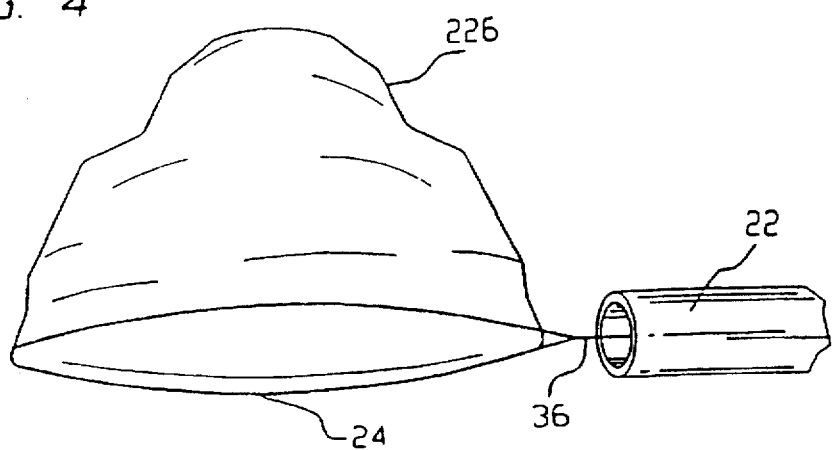
Figure 5:
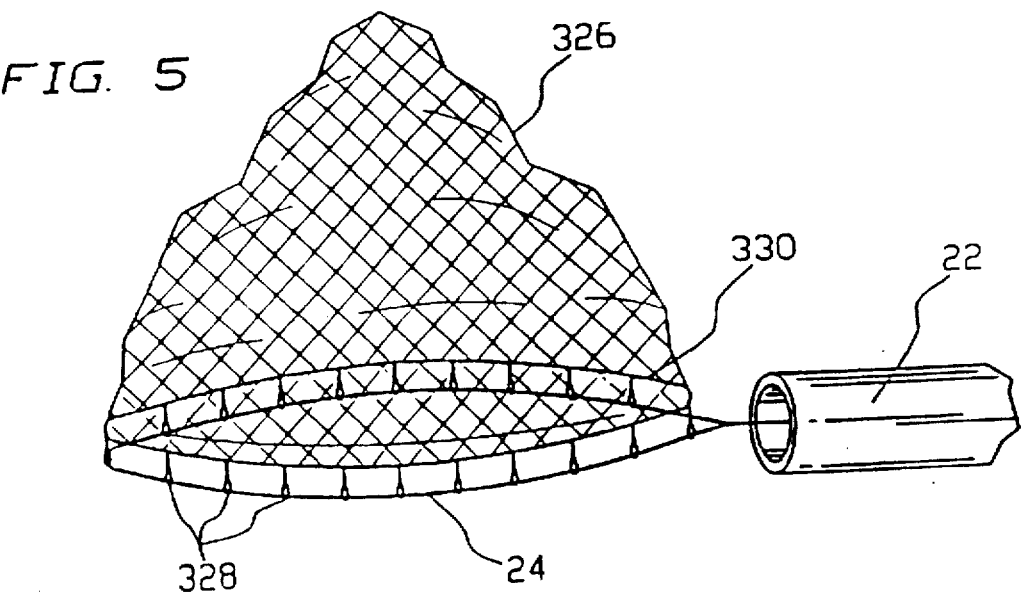
Figure 6:
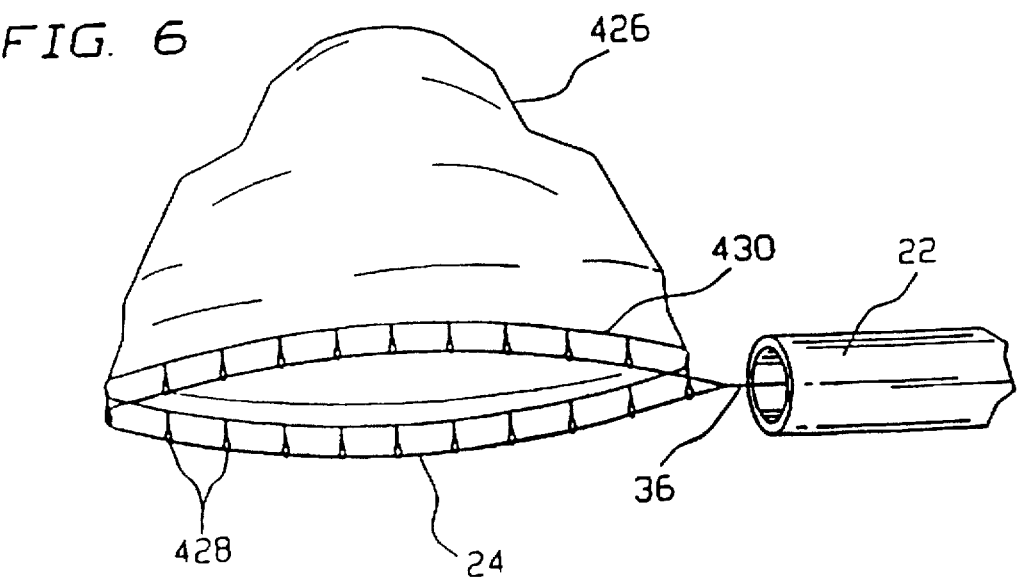

In FIGS. 3–6, like structural components bear the same reference designations. FIG. 3 shows a capture web 126 in the form of a net fastened directly to loop 24, while FIG. 4 shows a capture web 226 in the form of a continuous or solid transparent film fastened directly to loop 24. FIG. 5 illustrates a capture web 326 in the form of a net attached to loop 24 via a multiplicity of spaced ringlets 328. Loop 24 passes through ringlets 328, which are connected to a ring-shaped rim element 330 of web 326. Ringlets 328 are preferably made of a metallic material to facilitate the transmission of electrical current from cauterization loop 24 to the tissues of a polyp. FIG. 6 shows a capture web 426 in the form of a continuous or solid film of transparent polymeric material attached to loop 24 via a multiplicity of spaced ringlets 428. Loop 24 passes through ringlets 428, which are connected to a ring-shaped rim element 430 of web 426.

Figure 7:
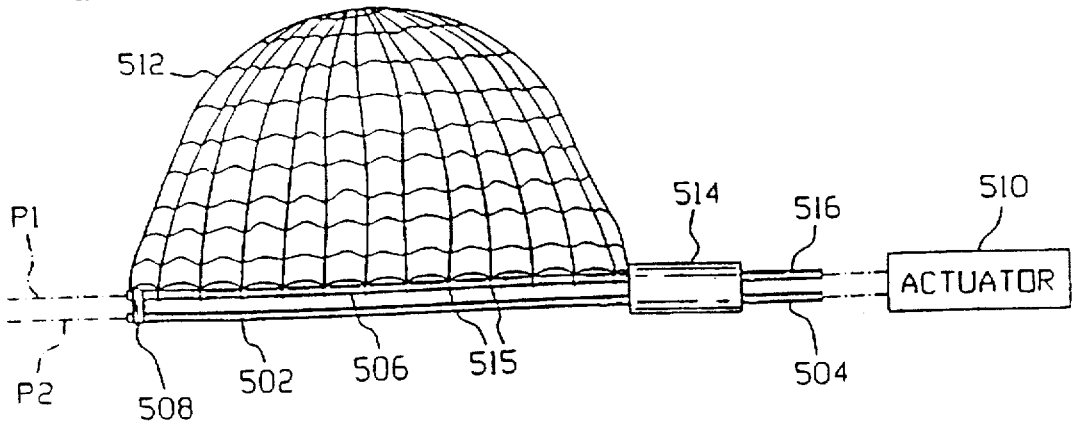
FIG. 7 is a schematic side elevational view, on an enlarged scale, of another embodiment of a snare cauterization instrument assembly, showing a pocket-defining web member on an auxiliary loop.

As illustrated in FIG. 7, a snare cauterization instrument assembly comprises a flexible cauterization loop 502, an electrical conductor 504 operatively connected to the cauterization loop for feeding an electrical current thereto, and a flexible auxiliary loop 506 connected via a fastening element 508 to the cauterization loop only at a distal end thereof. An actuator 510 is operatively connected to cauterization loop 502 and auxiliary loop 506 for alternately expanding and contracting the two loops in tandem with one another. A flexible web member 512 in the form of a net (or a continuous transparent membrane) is connected to auxiliary loop 506 essentially around the circumference thereof to form a capture pocket, auxiliary loop 506 defining a mouth opening of the pocket. Preferably, net 512 is fixed to auxiliary loop 506 only at a distal end and a proximal end (inside a tubular sheath member 514) thereof, the remaining connections 515 being slidable.

Actuator 510 is connected to cauterization loop 502 via conductor 504, which functions in response to manipulations of actuator 510 to eject cauterization loop 502 from a collapsed storage position inside the distal end of tubular sheath member 514 and subsequently to pull cauterization loop 502 back into the sheath member. Actuator 510 is coupled to auxiliary loop 506 via a flexible wire or rod member 516 which like conductor 504 extends longitudinally through sheath member 514.

Figure 8:
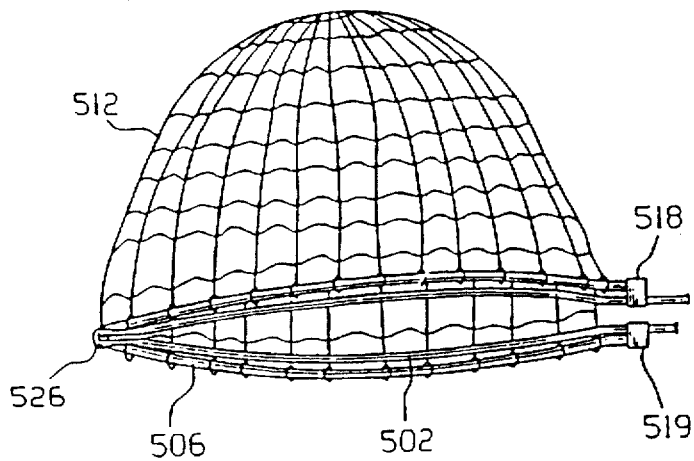
FIG. 8 is a schematic perspective view, also on an enlarged scale, of a modified snare cauterization instrument assembly, showing an auxiliary loop attached at three points to a cauterization loop.

Cauterization loop 502 and auxiliary loop 506 are disposed in parallel planes P2 and P1, respectively. As depicted in FIG. 8, auxiliary loop 506 may be connected at a proximal end to cauterization loop 502 at two points 518 and 519, as well as to the distal end of the cauterization loop. In that event, wire or rod member 516 may be omitted. As further shown in FIG. 8, auxiliary loop 506 is slightly larger than cauterization loop 502. The loops 502 and 506 are close, almost touching one another. As described above with reference to FIG. 7, web member 512 is fixedly connected to auxiliary loop 506 at a distal end and a proximal end thereof and slidably connected to the auxiliary loop between those ends.

Figure 9:
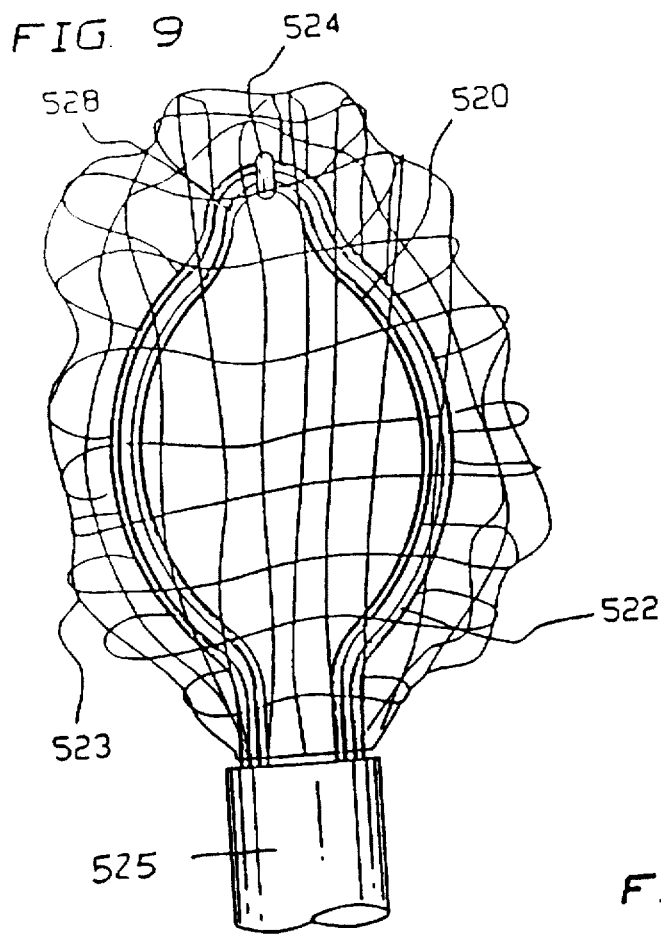
FIG. 9 is a schematic top view of another modified snare cauterization instrument assembly, showing an auxiliary loop attached at one point to a cauterization loop.

FIG. 9 shows a cauterization loop 520 and an auxiliary loop 522 connected to one another at a distal end via a fastener 524. Cauterization loop 520 and auxiliary loop 522 are essentially coplanar in the expanded configuration illustrated in FIG. 9. During an ejection stroke and a subsequent retraction stroke of cauterization loop 520 and auxiliary loop 522 in response to the manipulations of an actuator (not shown) at a proximal end (not shown) of the instrument assembly, cauterization loop 520 and auxiliary loop 522 expand and contract in unison in essentially a common plane.

The embodiments of a cauterization snare instrument assembly illustrated in FIGS. 7-9 are less expensive to manufacture than the ringlet embodiments of FIG. 5 and 6 and enable use of a wider range of materials for the pocket or web member (512 in FIG. 7) than the embodiments of FIGS. 3 and 4. In addition, a primary advantage of the particular dual loop embodiments of FIGS. 7–9 is that auxiliary loops 506 and 522 are not connected to the cauterization loops 502 and 520 along operative portions thereof, thereby eliminating any possible interference that the auxiliary loops or capture nets 512 and 523 (FIG. 9) might otherwise exhibit with respect to the cutting and cauterization operations.

As illustrated in FIGS. 8 and 9, this elimination of possible interference in the cutting and cauterization operations is furthered by forming cauterization loops 502 and 520 at their distal ends with respective tongue-like extensions 526 and 528 to which auxiliary loops 506 and 522 are connected. Extensions 526 and 528 may be coated with an insulating material (not illustrated) and serve to separate fasteners 508 (not shown in FIG. 8 for purposes of clarity) and 524 (FIG. 9) from the site of the cauterization procedure.

Auxiliary loops 506 and 522 are made of electrically nonconductive material preferably in the form of a synthetic resin or polymeric material such as polyethylene or nylon.

In using the snare cauterization instrument assemblies of FIGS. 7–9, cauterization loop 502 or 520 and auxiliary loop 506 or 522 are expanded from a collapsed configuration inside the distal end of sheath member 514 to an expanded configuration. In the expanded configuration, auxiliary loop 506 or 522 is preferably larger than cauterization loop 502 or 520 and essentially parallel thereto. A special case of parallelism is found where the cauterization loop and the auxiliary loop are coplanar.

Pursuant to additional steps in the procedure, pocket or web member 512 or 523 is opened during the expansion of cauterization loop 502 or 520 and auxiliary loop 506 or 522 and the expanded loops are passed over a selected polyp or other internal tissue agglomeration to be removed, so that web member 512 or 523 substantially surrounds the polyp. Cauterization loop 502 or 520 is then closed by pulling it into the distal end of sheath member 514 or 525 (FIG. 9). The closure of cauterization loop 502 or 520 around a base region of the polyp while the cauterization loop is energized with electrical current serves to severe the polyp at its base. Maintaining web member 512 or 523 surrounding the polyp during the cauterization procedure serves to capture the severed polyp at the instant of its severance.

Figure 10:
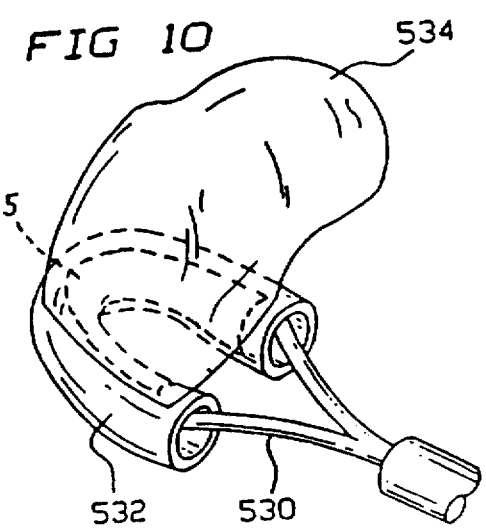
FIG. 10 is a schematic partial perspective view, on an enlarged scale, of an additional snare cauterization instrument assembly.

As illustrated in FIG. 10, a modified snare cauterization assembly includes a cauterization loop 530 surrounded along a substantial portion of its length by a tubular jacket or sleeve 532 to which a flexible pocket-defining web member 534 is connected. Jacket or sleeve 532 is made of a heat-conductive and electricity-conductive material enabling cauterization to proceed through the medium of the sleeve. In addition, sleeve 532 is provided with a coating or layer 535 of a biocompatible dye or ink material of a predetermined color. Color from coating 535 is transferred from the cauterization loop and particularly from sleeve 532 during the conduction of current through the loop. Coating 535 may be a liquifiable solid or a powder. Such a color-transferable coating or layer may be provided directly on any of the cauterization loops described herein. The deposition of a common color on a severed polyp and an unsevered neck or base area serves to facilitate a locating of the polyp's original situs upon a subsequent identification of the polyp as being malignant or a carcinoma. This is especially advantageous where several polyps are caught in the same procedure (see FIG. 15).

Figure 11:
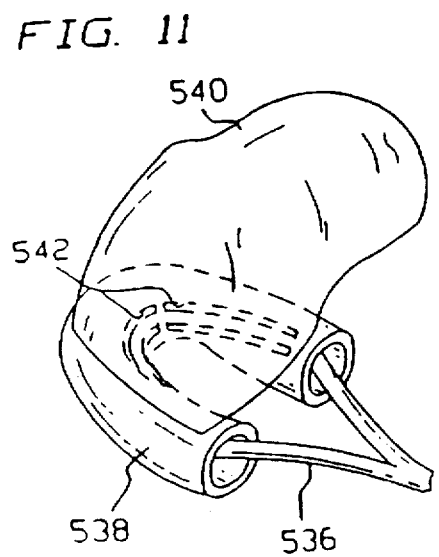
FIG. 11 is a schematic partial perspective view, on an enlarged scale, of yet a further snare cauterization instrument assembly.

As illustrated in FIG. 11, another modified snare cauterization assembly comprises a cauterization loop 536 enclosed along essentially its entire length by a tubular jacket or sleeve 538 to which a flexible pocket-defining web member 540 is coupled. Sleeve 538 is provided along an inner side with a plurality of longitudinally extending windows 542 for facilitating or enabling the conduction of heat and/or electrical current from cauterization loop 536 to organic tissues of a polyp or other cell mass to be removed from a patient's body.

Figure 12:
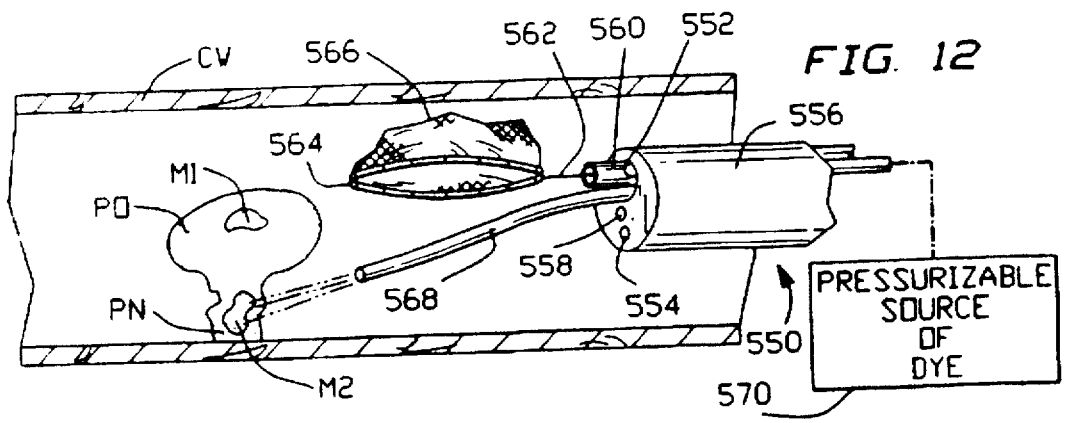
FIG. 12 is a schematic partial cross sectional view of a patient's colon with a polyp, showing a snare cauterization instrument assembly inserted through the biopsy channel of an endoscope which is itself inserted into the patient's colon, and further showing an instrument for depositing color markers on organic tissues.

As shown in FIG. 12, a surgical instrument assembly for use in a snare cauterization operation comprises an endoscope assembly 550 including a biopsy channel 552 and a light outlet 554 at a distal end of an endoscope insertion member 556 for delivering light to a surgical site inside a patient. The distal end of the endoscope insertion member 556 is further provided with a light inlet 558 for receiving light reflected from a surgical site. Light outlet 554 and light inlet 558 are located at the distal ends of a fiber optic illumination guide (not shown) and a fiber optic image guide (not shown), respectively, which extend longitudinally through endoscope insertion member 556.

As further illustrated in FIG. 12, a tubular sheath member 560 is inserted through biopsy channel 552, while a metal wire 562 passes longitudinally through the sheath 560 and is operatively connected at a distal end to an alternately expandable and collapsible metallic cauterization loop 564. An electrical supply (not shown in FIG. 12) is operatively connected to wire 562 for feeding an electrical current to loop 564 via the wire. A manually actuatable shifter (not illustrated in FIG. 12) is operatively connected to wire 562 at a proximal end thereof for longitudinally sliding the wire along sheath 560 in alternately opposite directions. A flexible web member 566 is connected to loop 564 to form a capture pocket, the loop defining a mouth opening of the pocket. Web member 566 is attached to loop 564 in a manner so as to expose the loop to enable effective cauterization of organic tissues by the loop.

Also extending through biopsy channel 552 is a tubular member 568 connected at a proximal end to a pressurizable dye or color source 570 such as a hypodermic syringe filled with a biocompatible liquid of a predetermined hue. A distal end portion of tubular member 568 is ejected from biopsy channel 552 upon arrival of the distal end of endoscope assembly 550 at an internal surgical site where a polyp PO is detected via light outlet 554 and light inlet 558 of endoscope assembly 550. Colored fluid is squirted from tubular member 568 to place recognizable markers M1 and M2 on polyp PO and a lower portion of a polyp neck PN by which polyp PO is connected to a colon wall CW of a patient. Markers M1 and M2 enable subsequent identification of the original location of polyp PO upon a medical analysis of the polyp after it has been severed and removed from the patient in accordance with procedures described herein and other steps known to those skilled in the art.

Upon an insertion of endoscope insertion member 556 into a patient's colon, endoscope assembly 550 is used to visually monitor internal body tissues of the patient, including the internal surface of colon wall CW. Upon detecting selected internal body tissues (e.g., polyp PO) to be removed from the patient, loop 564 and web member 566 are ejected from a distal end of biopsy channel 552. Loop 564 and web member 566 are at least partially expanded from a collapsed configuration upon their ejection from biopsy channel 552. Loop 564 is manipulated from outside of the patient, e.g., via endoscope assembly 550 and more particularly via wire 562 or sheath 560, to pass the expanded loop over the polyp PO so that web member 566 substantially surrounds the polyp. Subsequently, loop 564 is closed to engage the polyp PO around a base region thereof. Closure is effectuated by sliding sheath 560 in a distal direction so that a proximal part of loop 564 is retracted into the sheath. An electrical current is conducted through the closed or partially closed loop 564 to burn through the base region of polyp PO, thereby severing the polyp PO at the base region. Loop 564 is closed further upon a completed burning of the loop through the base of the polyp PO, thereby capturing the severed polyp in web member or pocket 566.

Polyp PO and neck PN may be marked with a biocompatible dye or ink by tubular member 568 prior to the cauterization procedure. Alternatively, at least the neck portion PN may be marked after polyp PO has been severed by loop 564 and captured in web member 566. Tubular member 568 operates to spray a determinable quantity of liquid dye or ink onto the surfaces of polyp PO and neck or base PN.

Figure 13:
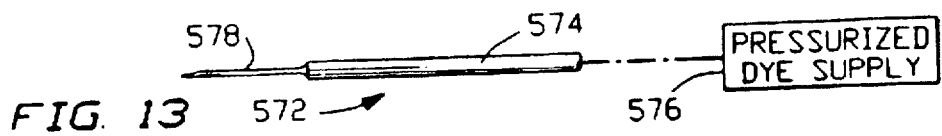
FIG. 13 is partially a schematic partial side elevational view and partially a block diagram of another color deposition instrument alternatively utilizable with the endoscopic snare cauterization instrument assembly of FIG. 12.

As illustrated in FIG. 13, another instrument 572 utilizable with endoscope assembly 550 to mark organic tissues inside a patient comprises a tubular member 574 operatively connected at a proximal end to a pressurized or pressurizable supply 576 of a biocompatible fluidic dye material. At a distal end, tubular member 574 is provided with a needle 578 for use in injecting the dye material below the surface of polyp PO and neck PN.

Figure 14:
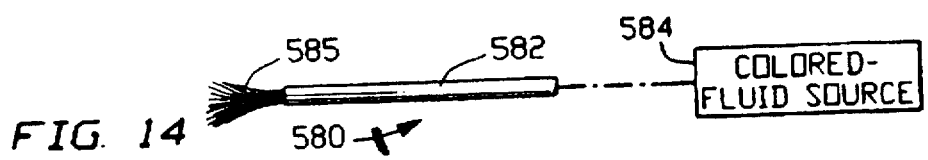
FIG. 14 is partially a schematic partial side elevational view and partially a block diagram of yet another color deposition instrument alternatively utilizable with the endoscopic snare cauterization instrument assembly of FIG. 12.

As shown in FIG. 14, another instrument 580 utilizable with endoscope assembly 550 to mark organic tissues inside a patient comprises a tubular member 582 operatively connected at a proximal end to a pressurized or pressurizable supply 584 of a biocompatible fluidic dye material. At a distal end, tubular member 582 is provided with a brush 585 for use in applying or painting the dye material on the surface of polyp PO and neck PN.

Figure 15:
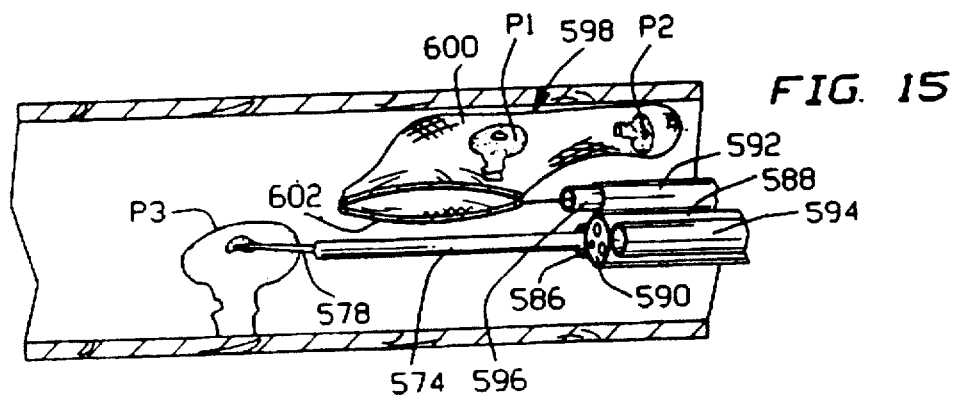
FIG. 15 is a schematic partial cross sectional view of a patient's colon with a polyp, showing a snare cauterization instrument assembly inserted through an alternately collapsible and expandable biopsy channel of an endoscope assembly which is itself inserted into the patient's colon, and further showing an instrument for depositing color markers on organic tissues.

Instrument 572 of FIG. 13 or instrument 580 of FIG. 14 may be inserted through biopsy channel 552 of endoscope assembly 550. Alternatively, tubular member 568 or marking instrument 572 or 580 may be inserted through an alternately expandable and collapsible biopsy channel 586 provided on a sheath 588 surrounding an endoscope insertion member 590, as illustrated in FIG. 15. Such an endoscope sheath 588 may take the form described and illustrated in U.S. Pat. Nos. 4,646,722 and 5,025,778, the disclosures of which are hereby incorporated by reference.

Sheath 588 is provided with other alternately expandable and collapsible biopsy channels 592 and 594, one of which receives a sheath 596 of a cauterization instrument assembly 598. As depicted in FIG. 15, an expanded web member 600 at a distal end of instrument assembly 598 carries a pair of polyps P1 and P2 which have already been marked with respective colors and severed. FIG. 15 shows a third polyp P3 being marked by instrument 572 (FIG. 13) prior to cauterization and severing by a loop 602 to which web member 600 is attached in a manner to enable cauterization by the loop.

Figure 16:
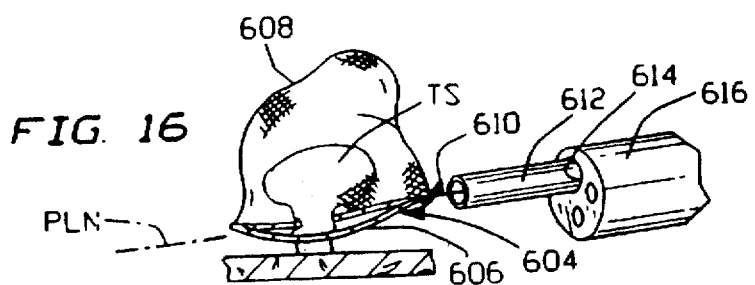
FIG. 16 is a schematic perspective view of a distal end portion of an endoscopic cauterization instrument assembly, showing a cauterization loop of the assembly in use to cauterize and sever a polyp in a patient's colon.

As shown in FIG. 16, another assembly for use in severing and removing an organic tissue sample TS from inside a patient comprises a cauterization loop 604 which in an expanded configuration has a bent configuration which arcs at 606 laterally from a plane PLN in which the loop opens and closes. Arc or curvature 606, inherent in the prestressed or spring-biased construction of loop 604, facilitates the capture of polyps by facilitating the encirclement thereof, as indicated in FIG. 16. The curved design of FIG. 16 may be used in any of the snare embodiments described herein, as well as in prior art cauterization loops without an attached capture pocket or web. Loop 604 is provided with a capture pocket 608 and is operatively connected to an electrical energy source (not shown) via an elongate wire 610 extending longitudinally through a sheath 612 in turn extending through a biopsy channel 614 of an endoscope insertion member 616.

It is to be noted that colored staples may be used to mark a polyp and/or its base, the staples being applied via an endoscopic stapling instrument as disclosed in U.S. Pat. Nos. 5,015,249 and 5,049,153 and 5,156,609, the disclosures of which are hereby incorporated by reference. The staples may be applied to the base or neck of a severed polyp either before or after a cauterization procedure.

As illustrated in FIGS. 17 and 18, an endoscopic cauterization snare surgical instrument 700 comprises a tubular sheath member 702, an alternately expandable and contractible cauterization loop 704, and an electrically conductive wire 706 operatively connected to loop 704. Wire 706 is slidable longitudinally through sheath member 702. A flexible web member 708 in the form of a net or film is connected to loop 704 essentially around a circumference thereof to form a capture pocket. Loop 704 defines a mouth opening of the pocket which is attached to loop 704 in a manner so as to expose the loop to enable effective cauterization of organic tissues by the loop. Web member 708 is removably attached to loop 704 to enable a separation of web member 708 from loop 704 upon a proximally directed stroke of wire 706 at the termination of a cauterization operation.

A purse string 710 is attached to web member 708 along a ring shaped locus proximately to the mouth opening of the capture pocket, i.e., proximately to loop 704. A proximal end strand or strands 712 of purse string 710 are attached at 714 to wire 706, proximately to the distal end thereof. Alternatively, purse string end strands 712 may extend in a proximal direction entirely through sheath member 702 to the proximal end thereof.

Web member 708 is attached by adhesive 716 (FIG. 18) to loop 704, either at a plurality of discrete points 718 (FIG. 17) or along a continuous length of loop 704. It is contemplated that web member 708 is removably attached to loop 704 along a radially outwardly facing surface area 720 of loop 704 (FIG. 18).

As discussed above, web member 708 may be in the form of a net, or alternatively in the form of a continuous film of polymeric material.

In using the cauterization snare assembly 700 of FIGS. 17 and 18, loop 704 is ejected from a distal end of sheath member 702 which in turn is ejected from a biopsy channel 724 of a flexible endoscope 726. Upon ejection of loop 704, loop 704 and web member 708 are expanded from a collapsed configuration to an at least partially opened configuration, as shown in FIG. 19A. As further shown in that drawing figure, expanded loop 704 is passed over the selected internal body tissues ST to be removed, so that web member 708 substantially surrounds the selected internal body tissues ST. Subsequently, as illustrated in FIG. 19B, loop 704 is drawn back into the distal end of sheath member 702, thereby closing loop 704 around a base region BR of the selected internal body tissues, while web member 708 is maintained surrounding the selected internal body tissues ST (e.g., polyp). During the drawing of loop 704 back into sheath member 702, an electrical current is conducted through loop 704 to sever the selected internal body tissues at base region BR. In addition, web member 708 is detached from loop 704 during the drawing of loop 704 back into sheath member 702 so that web member 708 remains outside sheath member 702, as depicted in FIG. 19C. The mouth opening of web member 708 is closed during the severing operation to thereby capture the severed internal body tissues ST in web member 708.

Web member 708 is detached by being peeled away from loop 704 at a distal edge 728 of sheath member 702. The drawing of loop 704 back into the distal end of sheath member 702 draws the capture pocket into contact with distal edge 728. That contact forces the capture pocket or web member 708 from loop 704.

Loop 704 is pulled completely into sheath member 702 (FIG. 19C) upon the termination of a cauterization operation. Web member 708 and the captured internal body tissues remain outside of sheath member 702.

As illustrated in FIG. 20A, cauterization loop 704 with its attached web member or capture pocket 708 is inserted into the distal end of sheath member 702 by initially providing the sheath member with a flared distal end portion 730. Upon a pulling of wire 706 in a proximal direction through sheath member 702, capture pocket or web member 708 is gradually compressed into a collapsed configuration. When the loop 704 and web member 708 have reached the narrowed end of sheath member 702, as shown in FIG. 20B, flared end portion 730 is severed by a blade 732 and discarded.

The material of a capture pocket as described herein must be biocompatible and should be heat resistant as well. In addition, it is contemplated that the material of the capture pocket has a memory as well, so that when the cauterization loop and the capture pocket are ejected from the distal end of a sheath, the capture pocket springs open, ready for use.

FIGS. 21A and 21B depict another method for disposing cauterization loop 704 with its attached web member or capture pocket 708 in the distal end of sheath member 702. Loop 704 and web member or capture pocket 708 are wrapped in a thin film 734, as shown in FIG. 21A. The entire assembly, including loop 704, pocket 708 and film 734 is then slid into the distal end of sheath member 702, as shown in FIG. 21B. Film 734 may be bonded to the inner surface of sheath 702, for example, by heat, adhesive, or ultrasonic welding.

Figure 22:
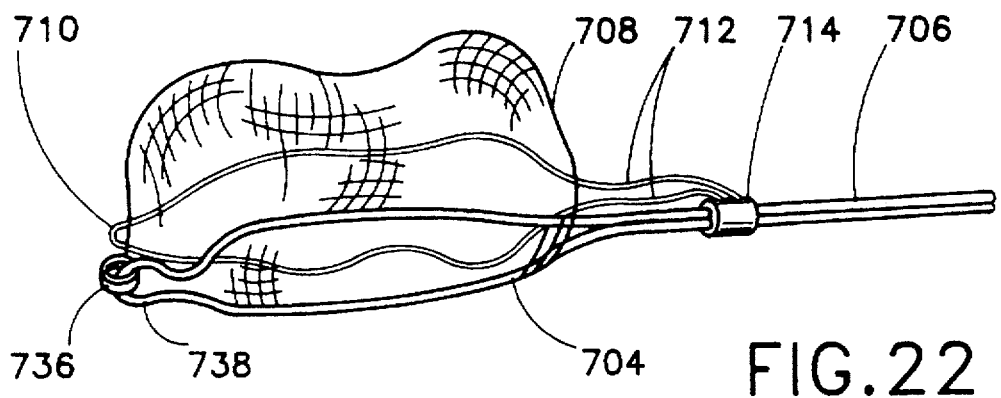
FIG. 22 is a schematic side elevational view, similar to FIG. 17, showing a modification of the snare assembly of that drawing Figure.
Figure 23:
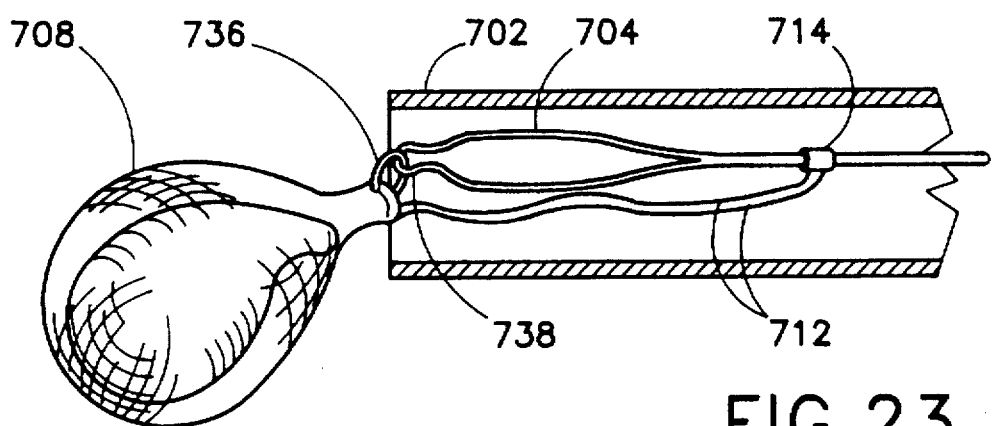
FIG. 23 is partially a cross-sectional view of a sheath and partially a side elevational view of the modified snare assembly of FIG. 22, at the termination of a polypectomy procedure.

As illustrated in FIGS. 22 and 23, web member or capture pocket 708 may be additionally provided, at a distal end only, with a permanent attachment 736 to cauterization loop 704, particularly at a distal finger-like extension 738 thereof. This permanent attachment may be in the form of a ringlet, a series of wound threads, a spot of adhesive, etc. Attachment 736 serves to facilitate insertion of loop 704 with pocket 708 into sheath 702 from the proximal end thereof. Attachment 736 prevents separation of capture pocket 708 from loop 704 during the insertion procedure and additionally provides extra assurance that the capture pocket will not become detached from loop 704 while inside the patient.

FIG. 23 shows a step at the termination of a polypectomy procedure, where capture pocket 708 is substantially separated from loop 704 but is retained thereon by virtue of attachment 736.

Figure 24:
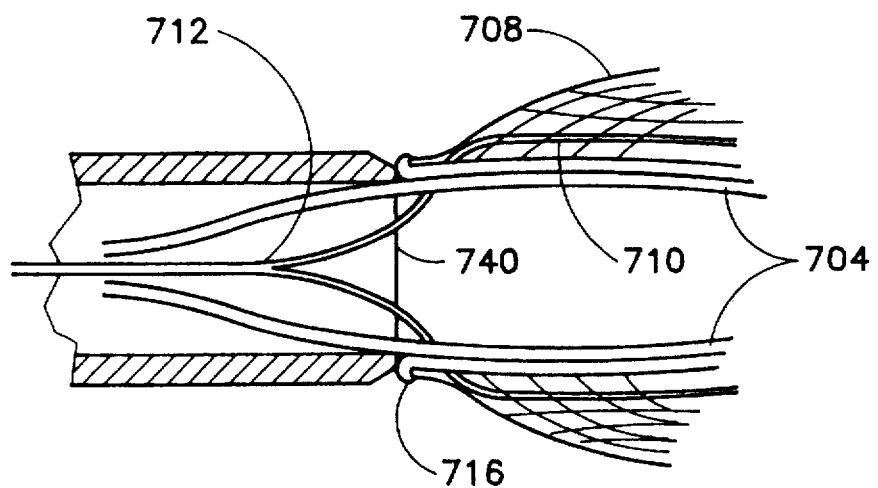
FIG. 24 is partially a cross-sectional view of a modified sheath and partially a side elevational view of the snare assembly of FIGS. 17, 18, and 19A–19C, showing an early stage in a retraction of loop 704 and pocket 708 into the sheath.

As depicted in FIG. 24, sheath 702 may be provided at a distal end with a sharp edge 740, formed by beveling the sheath. Edge 740 serves to facilitate separation of capture pocket 708 from loop 704 by cutting into adhesive 716 along radially outwardly facing surface area 720 of loop 704 (see FIG. 18).

Figure 25A:
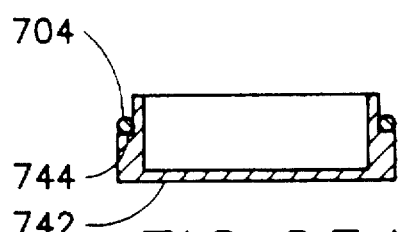
FIGS. 25A–25C are schematic cross-sectional views of a cauterization loop holder, showing successive steps in a manufacturing process.
Figure 25B:
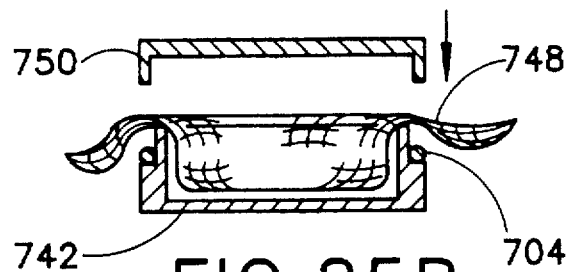
Figure 25C:
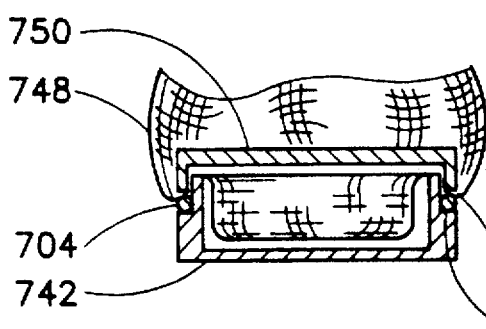

In manufacturing a cauterization snare as described above, loop 704 is placed around a cylindrical container or holder 742 so that a radially inward facing surface portion of the loop is in contact with the holder, as shown in FIG. 25A. Holder 742 has a circular shoulder 744 along a cylindrical outer surface. Shoulder 744 serves to support loop 704 in a predetermined position. A knitted net or web 748 is then pushed into holder 742, as shown in FIG. 25B, to provide extra material to form a pocket. A cap 750 is placed over the container, as indicated in FIGS. 25B and 25C. Net 748 is folded back from the edge of cap 750 (FIG. 25C), thereby positioning the net material a predetermined distance from shoulder 744, and accordingly from loop 704. An adhesive or polymeric material such as PARYLENE from a reservoir or source 751 is applied, e.g., sprayed, via a nozzle 752 or other applicator into a gap 754 between loop 704 and the folded back flap of net material 748. The adhesive or polymeric material such as PARYLENE sticks to the loop 704 and the net material, but not to the container or holder. After application of the adhesive or polymeric material, excess net material is cut off along a circular arc and the loop with the attached pocket is removed from the container or holder.

Figure 26:
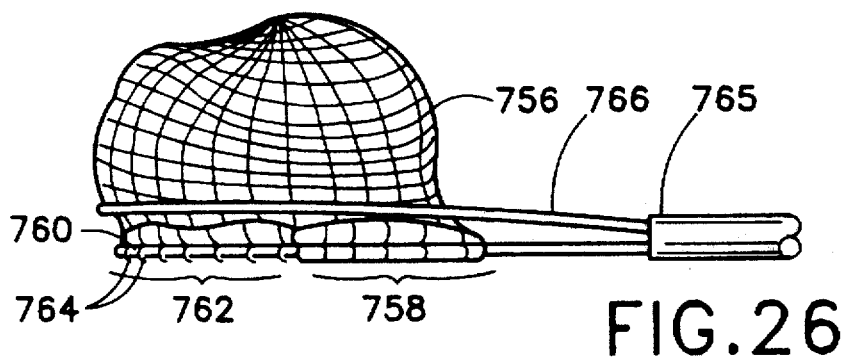
FIG. 26 is a schematic side elevational view of a modified cauterization snare with capture pocket, showing a cauterization loop and a pocket completely extended from a tubular sheath.
Figure 27:
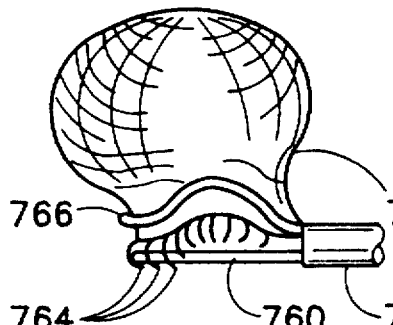
FIG. 27 is a schematic side elevation view of the modified cauterization snare and capture pocket of FIG. 26, showing partial retraction of the loop into the sheath and a concomitant dissociation of the capture pocket from the loop.

As depicted in FIG. 26, a capture pocket 756 is connected along a proximal side 758 of a cauterization loop 760 via a polymeric adhesive such as PARYLENE (not designated). Capture pocket 756 is connected along a distal side 762 of loop 760 via a plurality of filaments 764. During a polyp cauterization procedure as described hereinabove, pocket 756 is separated from the proximal side 758 of loop 760 owing to a peeling away of the polymeric adhesive layer during a retraction of loop 760 into the distal end of a sheath 765. This peeling away of the adhesive layer, and the concomitant partial dissociation of pocket 756 from loop 760, occurs generally before the conduction of current through loop 760 and the consequent severing of a polyp. During a later stage of the polyp severing and retrieval procedure, filaments 764 are burned off of cauterization loop 760, as shown in FIG. 27. Pocket 756 accordingly separates from loop 760 during the cauterization procedure. Pocket 756 is maintained in a closed state, holding a captured polyp (not shown), by virtue of a purse string 766, which functions as described hereinabove with reference to FIGS. 17 through 19C.

In an alternate configuration, pocket 756 may be connected to loop 760 solely by filaments 764 which are burned off or otherwise severed during a cauterization operation, thereby freeing the capture pocket from loop 760.

Figure 28:
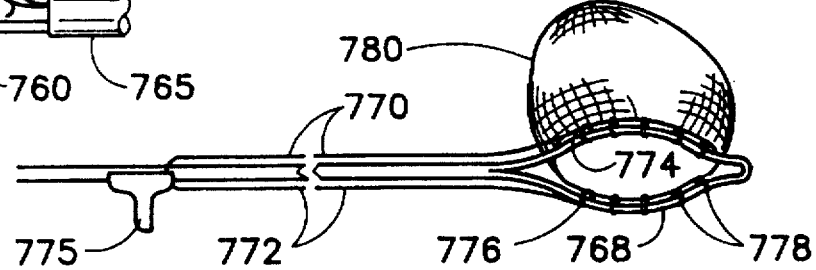
FIG. 28 is a schematic perspective view of another cauterization loop with a capture pocket.

FIG. 28 illustrates an embodiment of a cauterization snare which provides the possibility of repeated ejections and retractions of a cauterization loop 768 relative to a sheath (not illustrated) prior to a cauterization and severing of a polyp. This provides the practitioner with the capability of adjusting the location of the snare on a target polyp prior to completing the surgical severing operation. As illustrated in FIG. 28, two threads 770 and 772 are connected at their respective proximal ends to a slider member 775 which is disposed on a handle (not illustrated) of the snare. At their distal ends, threads 770 and 772 are connected to respective ringlets 774 and 776 which are slidably coupled to loop 768 proximally of other ringlets 778.

Upon a retraction of loop 768 and a consequent sliding of ringlets 774, 776, 778 along the loop to a distal side thereof after a surrounding of a polyp (not shown) with a capture pocket 780 on loop 768, the practitioner may decide that loop 768 is not optimally positioned on the neck of the polyp. Loop 768 is then ejected again from its sheath. In order to open pocket 780 and properly position the pocket along loop 768, the practitioner shifts slider member 775 in the proximal direction and thereby pulls ringlets 774 and 776 back towards the proximal end of loop 768.

Figure 29A:
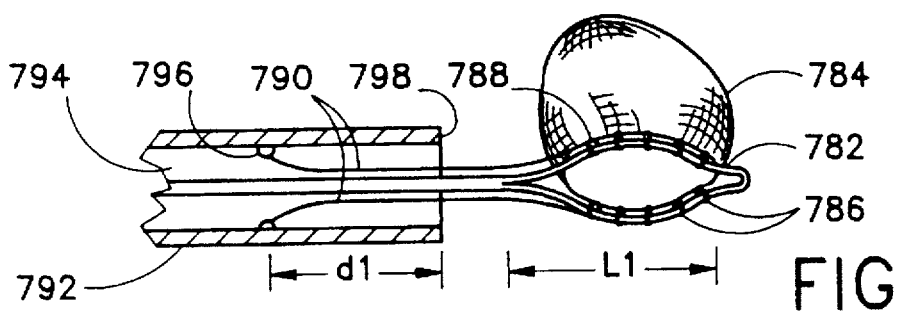
FIGS. 29A–29C are schematic side perspective views, partially in cross-section, of another modified cauterization snare and capture pocket, showing three steps in the use of the device.
Figure 29B:
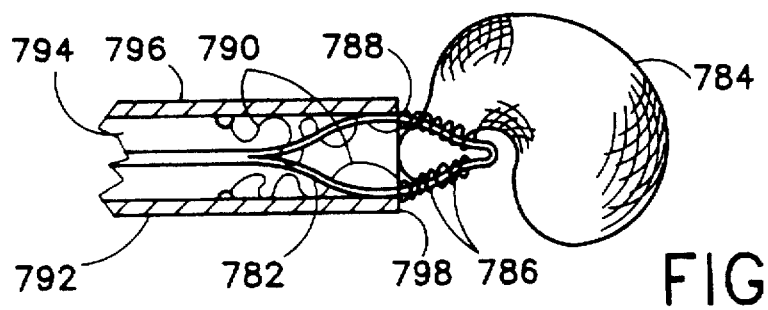
Figure 29C:
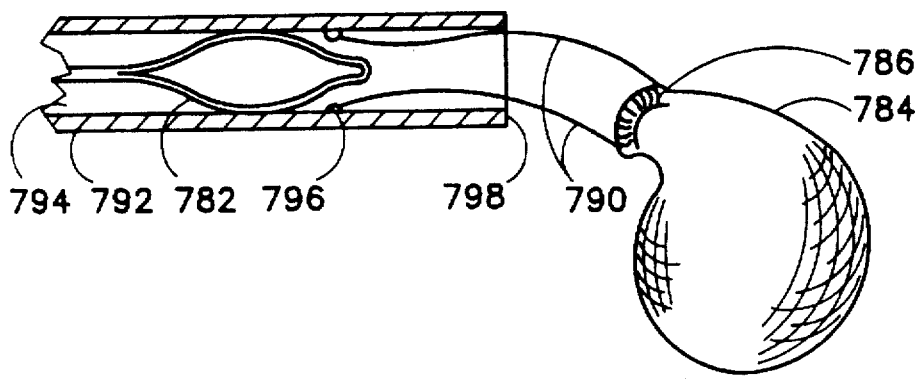

FIGS. 29A-29C illustrate steps in using a modified snare including a cauterization loop 782 with a capture pocket 784 attached by burnable ringlets 786 to the loop. The two most proximal ringlets 788 are connected via respective threads 790 to an inner surface or side 794 of a deployment sheath 792. Points of connection 796 of threads 790 to sheath surface 794 are located at a distance dl from the distal tip 798 of sheath 792 approximately equal to half of the length L1 of loop 782.

Upon an extension of loop 782 from sheath 792, as illustrated in FIG. 29A, threads 790 pull ringlets 788 in a proximal direction to the proximal side of loop 782, thereby stretching capture pocket 784 out to an optimally opened configuration. Of course, threads 790 also limit the extent to which loop 782 may be distanced from the distal end of sheath 792.

FIG. 29B shows the sliding of ringlets 786 and 788 in a distal direction relative to loop 782 upon a retraction of the loop into sheath 792, after loop 782 and pocket 784 have been placed about a polyp (not shown). In the event that the user endoscopist decides that an adjustment of the snare relative to the polyp is desired, loop 782 is pushed in a distal direction relative to sheath 792. This movement may be accomplished, of course, by pulling sheath 792 in a proximal direction relative to loop 782. Upon a sufficient ejection of loop 782 from sheath 792, threads 790 again pull ringlets 788 in a proximal direction to the proximal side of loop 782 to thereby open capture pocket 784.

If the user endoscopist decides that loop 782 is propitiously positioned relative to the subject polyp, loop 782 is pulled further into sheath 792, as illustrated in FIG. 29C. Ringlets 786 and 788 are severed from loop 782 via a burning process, thereby freeing capture pocket 784 from loop 782. The polyp cauterization assembly of FIGS. 29A-29C may be provided with a purse string (not illustrated) as described above with reference to FIGS. 17-19C, for ensuring closure of capture pocket 784 upon completion of a polyp severing operation.

Figure 30:
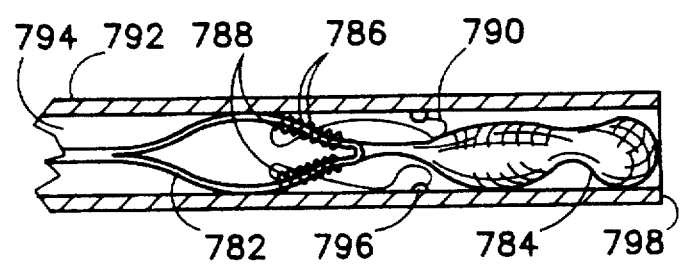
FIG. 30 is a schematic side elevational view, partially in cross-section, showing the cauterization snare and capture pocket of FIGS. 29A–29C in a retracted pre-firing insertion configuration.

As shown in FIG. 30, in packing loop 782 and pocket 784 inside sheath 792, pocket 784 may be disposed distally of loop 782, thereby facilitating the packaging process.

Figure 31:
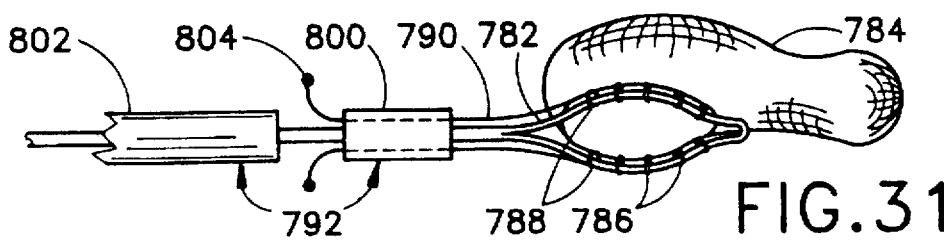
FIG. 31 is a schematic side elevation view showing a stage in the assembly of the cauterization snare and capture pocket of FIGS. 29A–29C and 30.

FIG. 31 illustrates a step in a manufacturing operation. Sheath 792 includes a distal segment 800 which is attached to a body portion 802 of the sheath via ultrasonic welding, adhesive, heating, or other process. Threads 790 extend through segment 800 and are sandwiched between segment 800 and body portion 802 upon connection of those sheath elements to one another. Threads 790 may be provided additionally with knots 804 which are located outside of the sheath 792 upon completion of manufacturing. Knots 804 serve as anchors, preventing dislodgement of threads 790 during use of the cauterization snare assembly.

Figure 32:
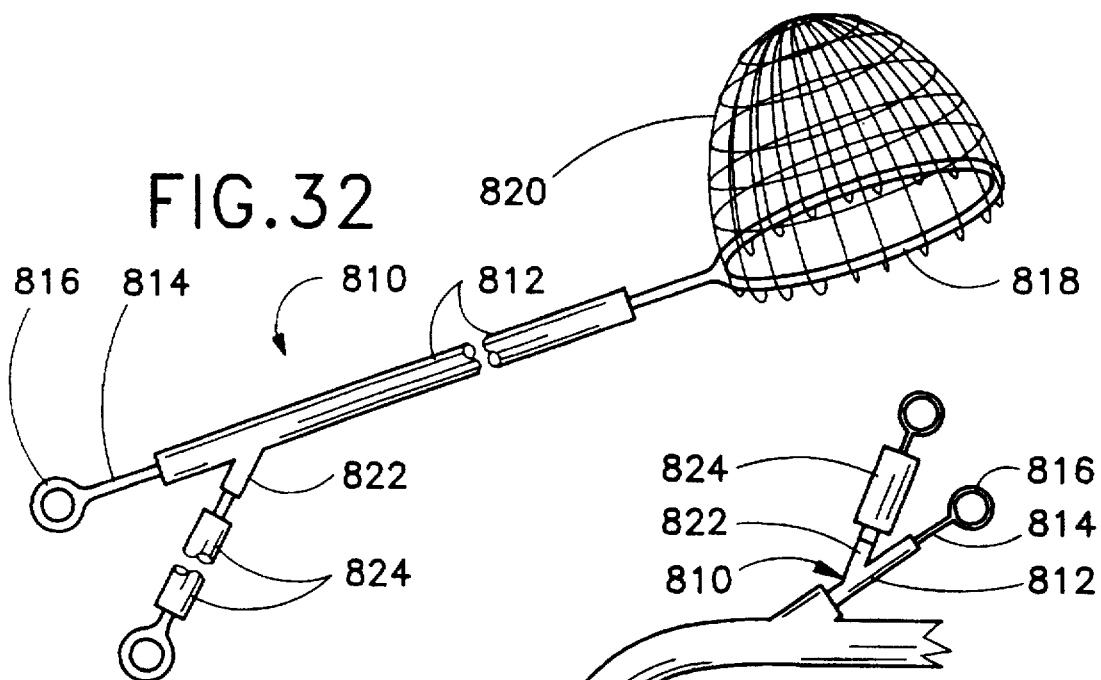
FIG. 32 is a schematic side elevational view of a snare device, for use in retrieving retained common bile duct stones.

As illustrated in FIG. 32, a surgical instrument assembly 810 for use in the retrieval of retained common bile duct stones comprises an elongate flexible tubular member 812 and an elongate rod or wire member 814 having a limited degree of flexibility, the rod being slidably inserted through the tubular member. Rod 814 is longer than tubular member 812 and is provided at a proximal end with a hand or finger grip 816 and at a distal end with a flexible loop 818 having a spring bias construction tending to form the loop into an opened configuration, as depicted in FIG. 32. Loop 818 is disposed in a collapsed configuration at least partially inside tubular member 812 distally of the distal end of rod 814 prior to a stone retrieval operation. A flexible web member 820 is connected to loop 818 to form a capture pocket. Loop 818 defines a mouth opening of the capture pocket. A port 822 is provided at a proximal end of tubular member 812 for connecting the tubular member to a pressurizable source of radio-opaque fluid such as a syringe 824.

Figure 33:
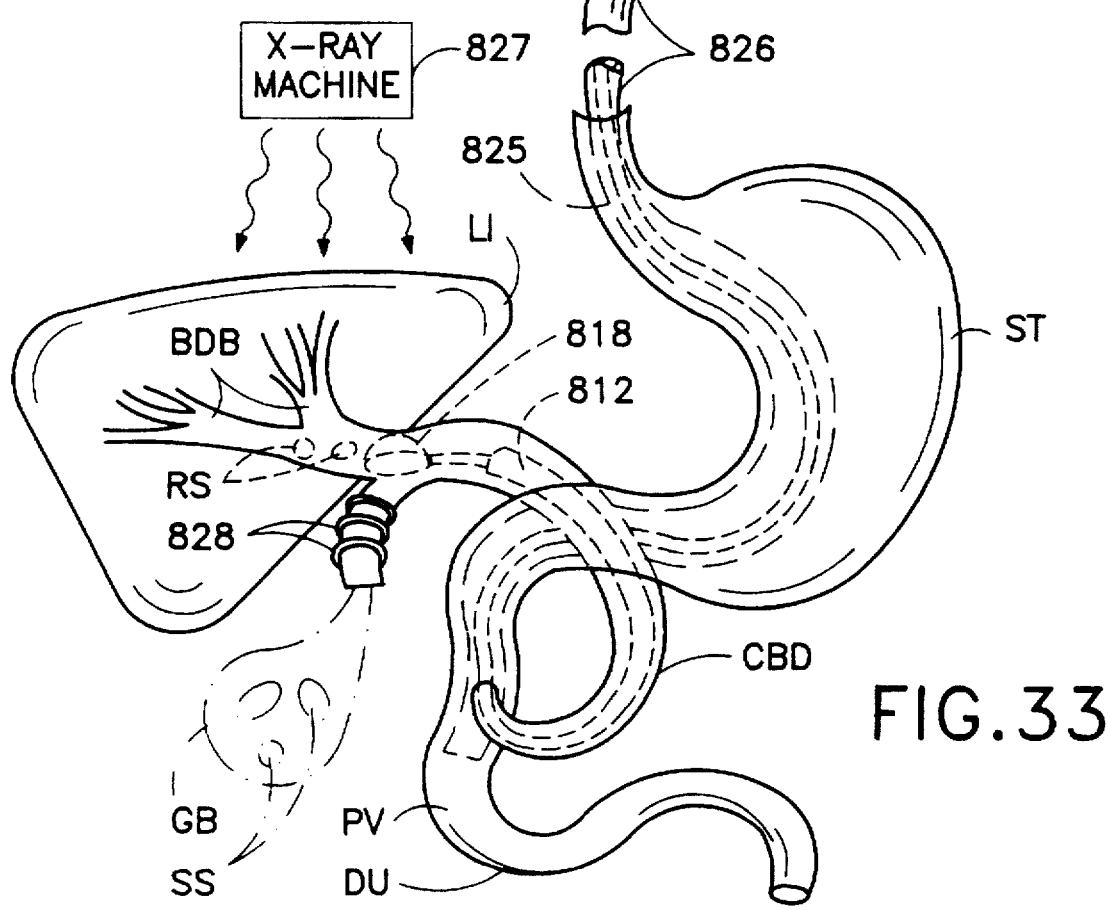
FIG. 33 is a schematic elevational view of portions of the digestive tract, showing use of the snare device of FIG. 32 in conjunction with an endoscope.

In order to be used in conjunction with an endoscope 826, as illustrated in FIG. 33, tubular member 812 is sufficiently narrow to fit down the biopsy channel of the endoscope. Endoscope 826 is inserted through the mouth (not shown) of a patient and through the stomach ST into the duodenum DU. Upon visually detecting, via endoscope 826, the Ampulla of Vater PV at the lower end of the common bile duct CBD, a surgeon pushes tubular member 812 in a distal direction through the biopsy channel so that the tubular member emerges from the distal end of the biopsy channel and enters common bile duct CBD through the Ampulla of Vater PV.

Upon a sufficient insertion of tubular member 812 into common bile duct CBD, source 824 of radio-opaque fluid is pressurized to dispense the fluid out the distal end of tubular member 812 into the common bile duct. X-ray equipment (not illustrated) is then used in a conventional procedure to locate retained stones RS in the common bile duct CBD. Subsequently, hand or finger grip 816 is manipulated to push rod 814 in a distal direction through tubular member 812 to eject loop 818 and web or pocket 820 from the tubular member and into the common bile duct CBD. Upon ejection, loop 818 and pocket 820 automatically expand, under the spring biased action of the loop, from a collapsed storage configuration to an opened use configuration. Finger grip 816 and tubular member 812 are then manipulated to capture the retained common bile duct stones RS. Upon capture of the stones RS, hand or finger grip 816 is pulled in the proximal direction to at least partially retract loop 818 and pocket 820 into the distal end of tubular member 812, thereby at least partially contracting the loop and the pocket to entrain and hold the retrieved stones RS. Subsequently, tubular member 812 is pulled in the proximal direction relative to endoscope 826 to remove the tubular member from the common bile duct CBD and out through the Ampulla of Vater PV. The entire assembly, including endoscope 826, is then extracted from the patient.

FIG. 33 also shows, in dot-dash lines, a gall bladder GB and stones SS which have been removed in a cholecystectomy. Two staples or clips 828 have been attached to the cystic duct CD to close that duct. The liver LI is connected to the common bile duct CBD via bile duct branches BDB.

Figure 34:
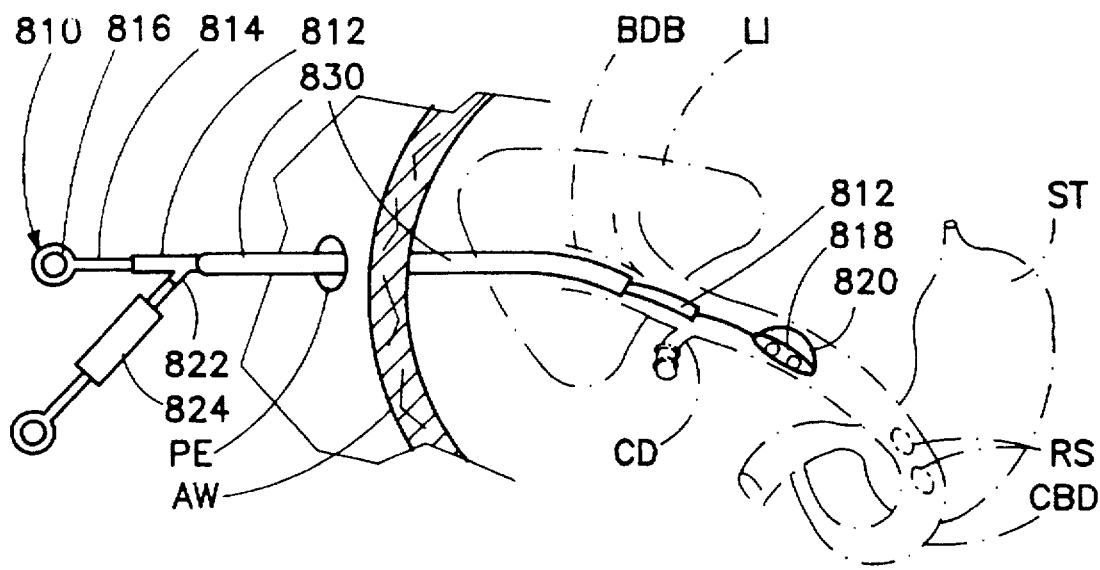
FIG. 34 is a schematic elevational view of portions of the digestive tract, showing another use of the snare device of FIG. 32.

FIG. 34 illustrates an alternative procedure using the snare device 810 of FIG. 32 to retrieve retained stones RS in common bile duct CBD subsequently to a cholecystectomy. A tubular port member 830 is disposed in the abdominal wall AW to traverse the wall. Tubular member 812 is dimensioned to be inserted through port member 830, as illustrated in FIG. 34. Port member 830 is inserted through abdominal wall AW and through a portion of liver LI into a selected bile duct branch BDB. To implement this procedure, a needle (not shown) is inserted inside the port member to pierce the abdominal wall AW, the liver LI and the selected-bile duct branch BDB. An expander or other device is used in a conventional technique to expand the path through the liver LI prior to the insertion of tubular member 812. Upon disposition of port member 830 as illustrated in FIG. 34, the needle is removed and replaced with snare device 810.

The remainder of the procedure is essentially the same as the method described hereinabove with reference to FIG. 33. Upon a sufficient insertion of tubular member 812 into common bile duct CBD, source 824 of radio-opaque fluid is pressurized to dispense the fluid out the distal end of tubular member 812 into the common bile duct. X-ray equipment (not illustrated) is then used in a conventional procedure to locate retained stones RS in the common bile duct CBD. Subsequently, hand or finger grip 816 is manipulated to push rod 814 in a distal direction through tubular member 812 to eject loop 818 and web or pocket 820 from the tubular member and into the common bile duct CBD. Upon ejection, loop 818 and pocket 820 automatically expand, under the spring biased action of the loop, from a collapsed storage configuration to an opened use configuration. Finger grip 816 and tubular member 812 are then manipulated to capture the retained common bile duct stones RS. Upon capture of the stones RS, hand or finger grip 816 is pulled in the proximal direction to at least partially retract loop 818 and pocket 820 into the distal end of tubular member 812, thereby at least partially contracting the loop and the pocket to entrain and hold the retrieved stones RS. Subsequently, tubular member 812 is pulled in the proximal direction relative to port member 830 to remove the tubular member from the common bile duct CBD and the selected bile duct branch BDB. The entire assembly, including port member 830, is then removed through wall AW.

Figure 35A:
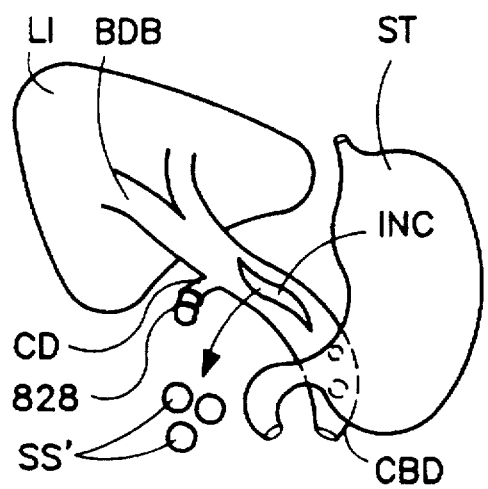
FIG. 35A is a schematic elevational view of portions of the digestive tract, showing an incision in the common bile duct made after a cholecystectomy.
Figure 35B:
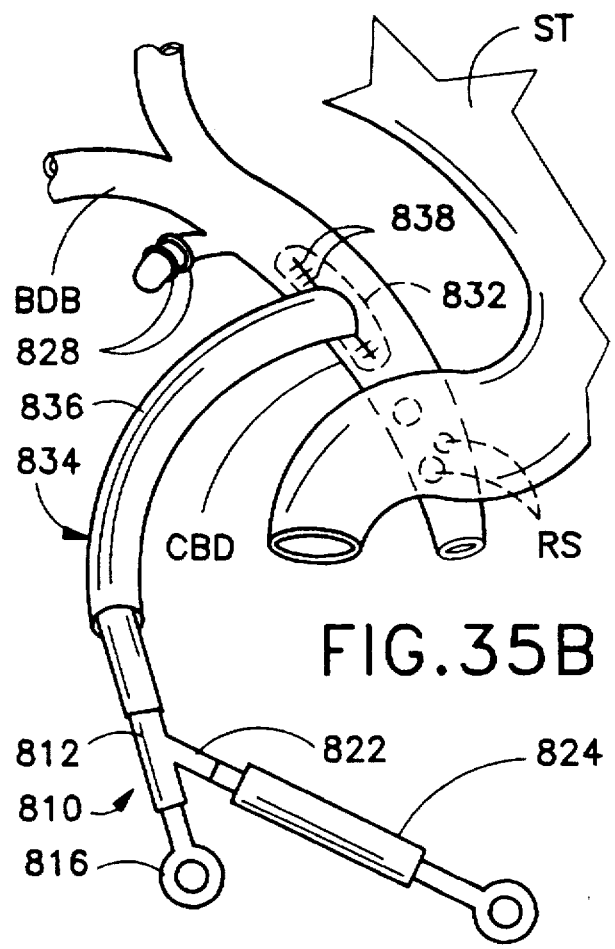
FIG. 35B is a schematic elevational view of portions of the digestive tract shown in FIG. 35A, illustrating a T-tube surgically inserted into the common bile duct and the snare of FIG. 32 inserted into the common bile duct via the T-tube.

FIGS. 35A and 35B depict another alternative procedure for retrieving retained stones RS in the common bile duct CBD. Upon completion of a cholecystectomy, wherein staples or clips 828 are clamped to the severed cystic duct CD, an incision INC is made in the common bile duct CBD. Any stones SS' visible in the duct are removed. A hollow cross-bar 832 of a T-tube 834 with an elongate hollow shaft 836 is then inserted into the common bile duct CBD through incision INC. Upon that disposition of cross-bar 832, incision INC is closed by sutures 838 (FIG. 35B). Shaft 836 is brought out through a perforation PE in the abdominal wall.

T-tube 834 is conventionally used to drain bile from the common bile duct CBD.

Upon the completed disposition of T-tube 834, snare device 810 is inserted through the T-tube and into the common bile duct CBD. Snare device 810 is then used as described hereinabove with reference to FIGS. 33 and 34 to remove retained common bile duct stones RS.

Figure 36:
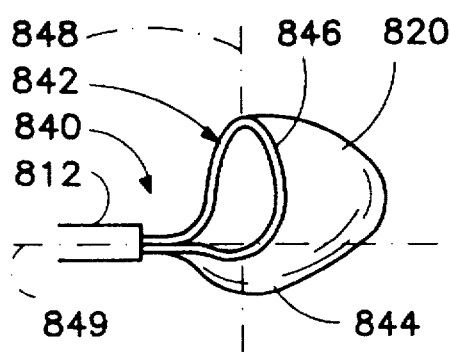
FIG. 36 is a partial side elevational view of a modified snare device.

As illustrated in FIG. 36, another snare device or instrument assembly 840 for use in retrieving retained common bile duct stones includes the same elements as described above with reference to FIG. 32 except that a flexible loop 842 has a spring bias construction tending to form the loop into an opened configuration having a bend 844 so that a portion 846 of the opened loop, upon an ejection from tubular member 812, defines a plane 848 oriented substantially orthogonally with respect to the tubular member at the distal end thereof. More particularly, loop 842 in the opened configuration lies essentially in two planes 848 and 849 oriented at an angle, preferably a right angle, with respect to one another. Prior to ejection during a stone retrieval procedure, loop 842 is disposed in a straightened and collapsed configuration at least partially inside tubular member 812. Web or pocket 820 is connected to loop 842 so that the loop defines a mouth opening of the pocket.

The loop of FIG. 36 is specifically adapted for use in retrieving retained common bile duct stones. The angled configuration of the loop 842 facilitates collection of stones within the narrow confines of the common bile duct. Loop 842 need only be moved in an axial or longitudinal direction through the common bile duct. Generally, loop 842 with its capture pocket 820 is moved away from the distal end of tubular member 812 towards retained stones.

As illustrated in FIG. 37A, a further snare device or instrument assembly 850 for use in retrieving retained common bile duct stones includes the same elements as described above with reference to FIG. 32 except that tubular member 812 of snare device 850 is additionally provided with cauterization componentry 852 for use in enlarging the opening of the common bile duct at the Ampulla of Vater. Cauterization componentry 852 includes a cauterization wire 854 extending longitudinally through tubular member 812 from an actuator handle 856 at a proximal end of the instrument, past an elongate window 858 to the distal tip 860 of tubular member 812. At distal tip 860, cauterization wire 854 is attached to tubular member 812. Accordingly, upon a pulling of wire 854 in a proximal direction via handle 856, a distal end portion of tubular member 812 which is roughly coextensive longitudinally with window 858 bends, as illustrated in FIG. 37B. Wire 854 emerges from tubular member 812 through window 858 and is energized with electrical current from a source 862 operatively connected to the wire.

Snare device 850 is used in conjunction with an endoscope, as described above with reference to FIG. 33. Upon ejection of a distal portion of tubular member 812 from the biopsy channel of the endoscope 826, handle 856 is pulled in the proximal direction, whereby wire 854 emerges through window 858, as shown in FIG. 37B. The distal end of tubular member 812 is then inserted through the Ampulla of Vater. Current from source 862 cuts and cauterizes the tissues of the Ampulla of Vater to enlarge the opening from the common bile duct CBD into the duodenum DU (FIG. 33). Upon completion of the enlarging procedure, handle 856 is pushed in the distal direction to straighten out the distal end portion of tubular member 812 and to retract wire 854 back into the tubular member through window 858. Tubular member 812 is then pushed into the common bile duct and hand or finger grip 816 manipulated to eject loop 818 and pocket 820, as illustrated in FIG. 37C. The procedure described hereinabove with reference to FIGS. 33 and 34 is then undertaken to retrieve retained stones.

As depicted in FIG. 38, another snare device or instrument assembly 870 includes a spring-biased loop 872 provided with a flexible capture pocket 874. An ancillary web 876 is attached to loop 872 and/or pocket 874 for forming a trap door. Retained common bile duct stones easily pass through an aperture 878 in web 76 to become lodged in capture pocket 874. However, the captured stones are unable to leave the capture pocket 874 once lodged therein, owing to the valve-type action of web 876. The snare device 870 of FIG. 38 is adapted for the removal of several stones in the same operation, without the necessity for removing and reinserting the instrument assembly to subsequently capture other stones.

Web 876 is cupped towards the inside of capture pocket 874 and is formed with a plurality of pleats or folds 879 which enable expansion of aperture 878 to accommodate inpassing stones. The pleats 879 resist inversion of web 876 outside of capture pocket 874.

FIG. 39 illustrates a modified snare device or instrument assembly 880 which includes a spring-biased loop 882 provided with a flexible capture pocket 884. A funnel-shaped ancillary web 886 is attached to loop 882 and/or pocket 884 and tapers inwardly into capture pocket 884. An inner end of funnel 886 is provided with a flap 887 which functions as a trap door to hold captured common bile duct stones inside pocket 884. Retained common bile duct stones easily pass through an aperture 888 defined by funnel 886 and become lodged in capture pocket 884. However, the captured stones are unable to leave the capture pocket 884 once lodged therein, owing to the valve-type action of flap 887.

Figure 40:
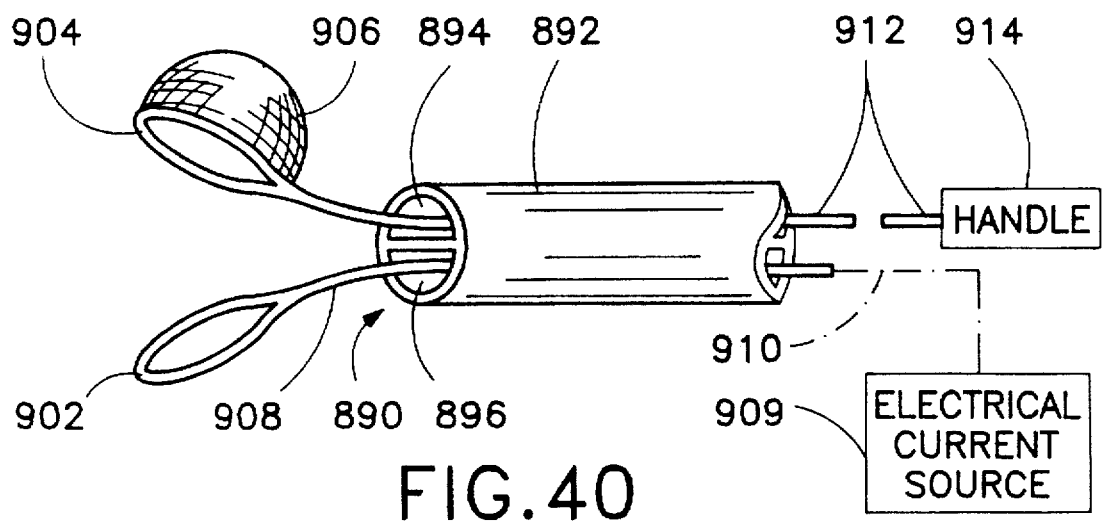
FIG. 40 is a schematic side perspective view, on an enlarged scale, of an endoscopic surgical instrument assembly in accordance with the present invention.

As illustrated in FIG. 40, a surgical instrument assembly 890 for use in snare cauterization operations comprises a tubular instrument guide member 892 defining a plurality of separate longitudinally extending lumens 894 and 896. Lumens 894 and 896 have semi-circular cross-sections. Tubular member 892 has a diameter sufficiently small so that the tubular member can be inserted through a biopsy channel 898 of a flexible endoscope insertion member 900 (FIGS. 41A–41E). Instrument assembly 890 further comprises a cauterization loop 902 and an auxiliary loop 904 which is provided with a flexible web member 906 defining an alternately expandable and contractible capture pocket. Auxiliary loop 904 defines a mouth opening of the pocket.

Figure 41A:
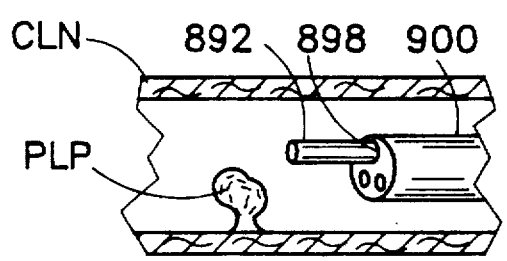
FIGS. 41A–41E are partially schematic cross-sectional views of a colon and partially schematic side perspective views of an endoscope incorporating the instrument assembly of FIG. 40, showing successive steps in the performance of an endoscopic operation in accordance with the present invention.

An electrically conductive wire 908 is connected to cauterization loop 902, cauterization loop 902 and wire 908 being disposed at least partially in lumen 896 of tubular member 892. An electrical supply 909 is operatively connected to wire 908 via a coupling 910 for feeding an electrical current to cauterization loop 902 via wire 908. An elongate flexible shifting member 912 (e.g., a wire) is connected at one end to auxiliary loop 904. Auxiliary loop 904 and wire 912 are at least partially disposed in lumen 894 of tubular member 892. A handle assembly 914 is provided at the proximal end of wire 912 for facilitating the maneuvering of auxiliary loop 904 from outside the patient. Handle assembly 914 may also be connected to cauterization loop 902 to facilitate the manipulation of the loop to eject the loop from lumen 896 and to place the loop about a polyp PLP (FIG. 41A). Handle assembly 914 is operatively connected to cauterization loop 902 and auxiliary loop 904 so as to allow those two elements to be ejected independently from tubular member or catheter 892.

Web member 906, whether a net or a continuous film of polymeric material, may be connected to auxiliary loop 904 at a plurality of spaced locations, e.g., via ringlets (not shown). Tubular member 892 is preferably flexible so that it may pass along bends in endoscope insertion member 900 upon a deployment thereof during an endoscopic investigation.

As depicted in FIG. 41A, upon introduction of endoscope insertion member 900 into a patient's colon CLN and use of the endoscope assembly to visually monitor internal body tissues of the patient to locate polyp PLP, tubular member 892 is moved in a distal direction through biopsy channel 898 of endoscope insertion member 900 to eject a distal end portion of the tubular member from the biopsy channel.

Figure 41B:
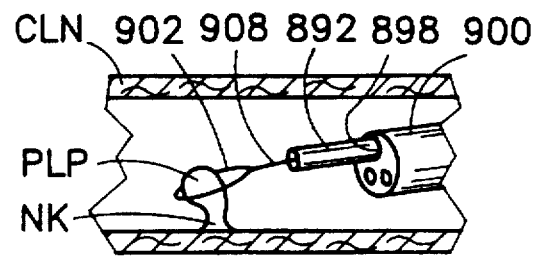

Subsequent steps of an endoscopic surgical procedure are depicted in FIG. 41B. Cauterization loop 902 is shifted in a distal direction relative to ejected tubular member 892 to eject the cauterization loop from the tubular member. Upon ejection, ejected cauterization loop 902 is expanded from a collapsed configuration inside tubular member 892 to an opened configuration. Cauterization loop 902 is then manipulated from outside of the patient to pass the expanded cauterization loop over polyp PLP which is to be removed from the patient.

Figure 41C:
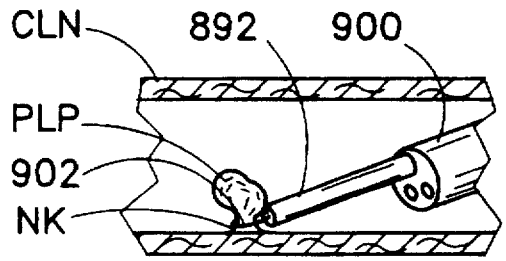

As illustrated in FIG. 41C, cauterization loop 902 is at least partially closed to engage polyp PLP around a base region or neck NK thereof. This closure is effectuated by shifting tubular member 892 and cauterization snare relatively towards one another to thereby at least partially withdraw or retract cauterization loop 902 into tubular member 892. Upon closure of cauterization loop 902 about polyp neck NK, an electrical current is conducted through wire 908 and cauterization loop 902 to burn through polyp PLP at base region or neck NK thereof, thereby severing the polyp at the neck.

Figure 41D:
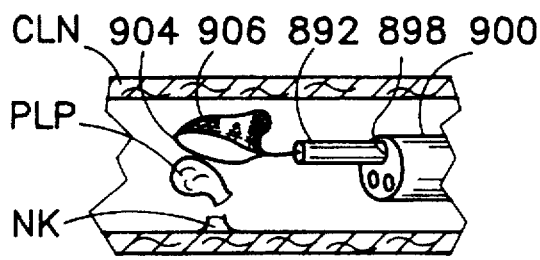
Figure 41E:
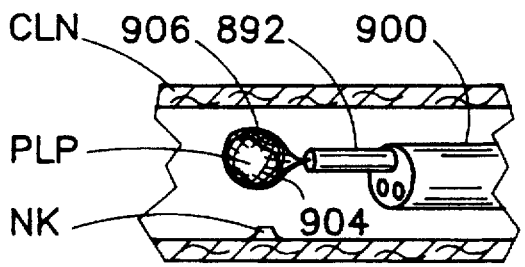

Upon a severing of the polyp PLP at the neck NK, cauterization loop 902 is retracted into tubular member 892. Then, auxiliary loop 904 is ejected from tubular member 892, the auxiliary loop and web member or capture pocket 906 being opened from a folded configuration inside lumen 94 of tubular member 892 to an at least partially expanded or opened configuration, as illustrated in FIG. 41D. Subsequently, auxiliary loop 904 is maneuvered from outside the patient to pass the opened auxiliary loop 904 over the severed polyp PLP so that web member or pocket 906 substantially surrounds the polyp. At that juncture, auxiliary loop 904 is at least partially closed to capture the severed polyp PLP in web member or pocket 906, as shown in FIG. 41E. As further indicated in FIG. 41E, the closing of auxiliary loop 904 includes shifting tubular member 892 and the auxiliary loop relatively towards one another to thereby at least partially withdraw auxiliary loop 904 into tubular member 892. After capture has been effectuated, polyp PLP is removed from the patient together with auxiliary loop 904 and the capture pocket 906.

Biopsy channel 898 of endoscope member 900 may be located in a sheath disposed on the endoscope, as described in U.S. Pat. No. 5,217,001, the disclosure of which is hereby incorporated by reference.

It is to be noted that the device or instrument assembly of FIG. 40 is similar to that of FIGS. 37A–37C insofar as both instrument assemblies include a cauterization wire disposed simultaneously with a separate capture pocket in a common tubular instrument guide member.

Figure 42A:
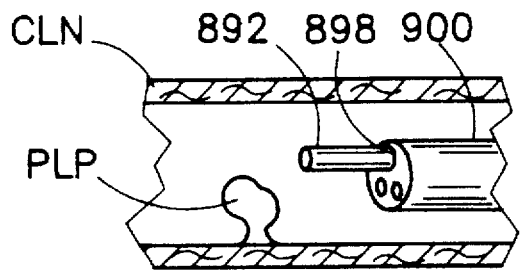
FIGS. 42A–42F are partially schematic cross-sectional views similar generally to FIGS. 41A–41E, showing an alternative series of successive steps in an endoscopic operation in accordance with the present invention.

FIGS. 42A–42E depict a sequence of steps in another endoscopic polyp removal procedure. FIG. 42A is identical to FIG. 41A and shows endoscope insertion member 900 inserted into colon CLN. Insertion member 900 is used to visually monitor internal body tissues of the patient to locate polyp PLP. Upon locating polyp PLP, the endoscopist moves tubular member 892 in a distal direction through biopsy channel 98 of endoscope insertion member 900 to eject the distal end portion of the tubular member from the biopsy channel.

Figure 42B:
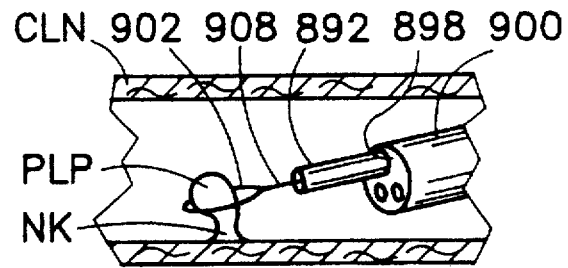

FIG. 42B is identical to FIG. 41B and illustrates subsequent steps of the endoscopic polyp removal procedure. Cauterization loop 902 is shifted in a distal direction relative to ejected tubular member 892 to eject the cauterization loop from the tubular member. Upon ejection, ejected cauterization loop 902 is expanded from a collapsed configuration inside tubular member 892 to an opened configuration. Cauterization loop 902 is then manipulated from outside of the patient to pass the expanded cauterization loop over polyp PLP which is to be removed from the patient.

Figure 42C:
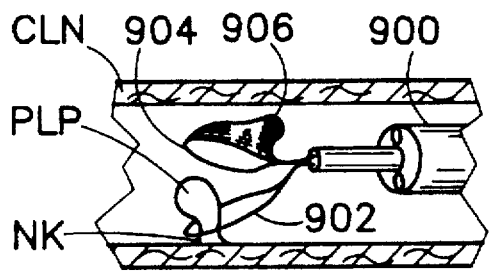
Figure 42D:
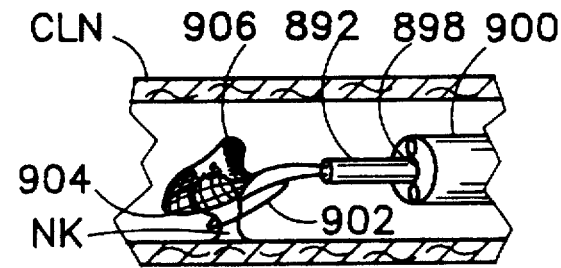
Figure 42E:
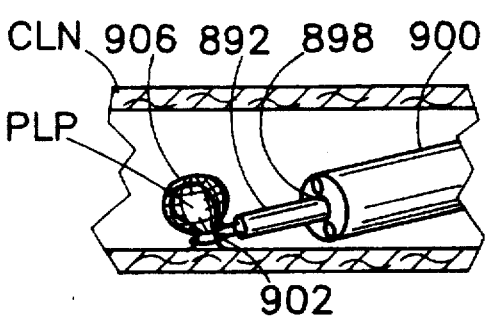

As illustrated in FIG. 42C, cauterization loop 902 is maneuvered to encircle polyp PLP around base region or neck NK thereof. Prior to completing a closure of cauterization loop 902 about polyp PLP, auxiliary loop 904 and capture pocket 906 are ejected from tubular member 892 and are opened from a folded configuration inside lumen 894 of tubular member 892 to an at least partially expanded or opened configuration. As illustrated in FIG. 42D, auxiliary loop 904 is then maneuvered from outside the patient to pass the opened auxiliary loop 904 and capture pocket 906 over the polyp PLP so that web member or pocket 906 substantially surrounds the polyp. At that juncture, tubular member 892 on the one hand and cauterization loop 902 and auxiliary loop 904 on the other hand are shifted relatively towards one another to thereby effectuate a partial closure of the loops about polyp PLP, particularly about neck region NK thereof, as shown in FIG. 42E.

Figure 42F:
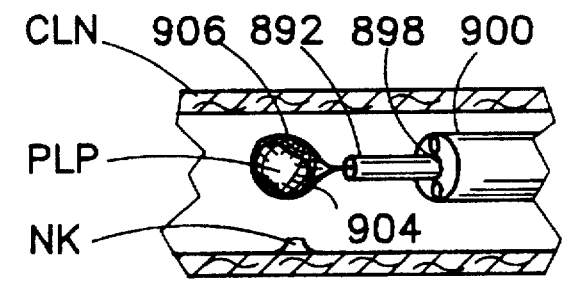

Upon closure of cauterization loop 902 about polyp neck NK, an electrical current is conducted through wire 908 and cauterization loop 902 to burn through polyp PLP at base region or neck NK thereof, thereby severing the polyp at the neck. Simultaneously with the current flow, cauterization loop 902 is drawn into tubular member 892. The severed polyp is automatically or naturally captured within pocket 906, as illustrated in FIG. 42F. After capture has been effectuated, polyp PLP is removed from the patient together with auxiliary loop 904 and the capture pocket 906.

Figure 43:
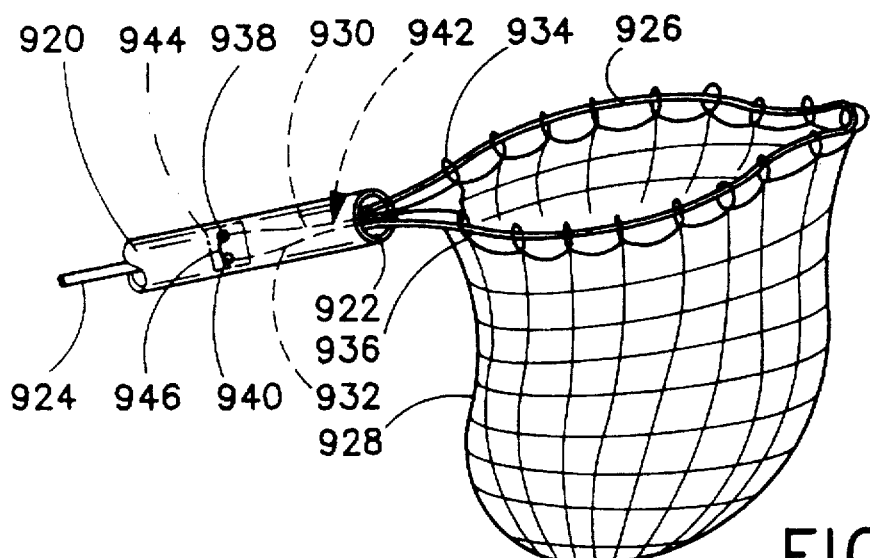
FIG. 43 is a schematic perspective view, on an enlarged scale, of a capture pocket or pouch in accordance with the present invention, showing the capture pocket or pouch in an opened configuration.
Figure 44:
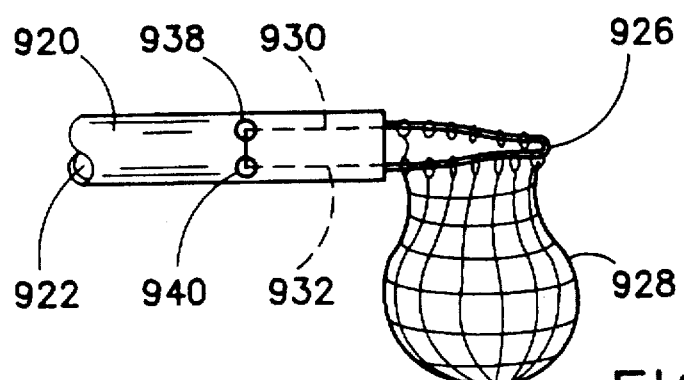
FIG. 44 is a side elevational view of the capture pocket or pouch of FIG. 43, showing the capture pocket or pouch in a substantially closed configuration.

FIGS. 43 and 44 illustrate an improvement in a loop and pouch assembly which may be incorporated into the assembly of FIG. 40. The assembly comprises a tubular member 920 defining at least one longitudinally extending lumen 922. Tubular member 920 has a diameter sufficiently small so that the tubular member can be inserted though a biopsy channel of a flexible endoscope. An elongate flexible shifting member 924 is connected at one end to a flexible loop 926, the loop and the shifting member being at least-partially disposable in lumen 922. A flexible web member 928 is connected to loop 926 so as to form a capture pocket or pouch. Loop 926 defines a mouth opening of pocket 928. At least one flexible tensile member or tether 930 and preferably two flexible tensile members 930 and 932 are connected to flexible web member or pocket 928 at proximal end points 934 and 936 thereof. Flexible tensile members 930 and 932 are also connected to tubular member 920 at a pair of holes 938 and 940 formed in tubular member 920 at points spaced from a distal end thereof. Tensile members 930 and 932 extend from flexible web member 928 into lumen 922 of tubular member 920.

Tensile members 930 and 932 are segments of a single flexible tensile tether member 942 which extends through holes 938 and 940 in tubular member 920. A patch 944 is disposed on an outer surface of tubular member 920 over holes 938 and 940 and over a bight portion 946 of tensile member 942 which is located outside the tubular member. Patch 944 is a thin film of polymeric material which is heat shrunk tightly over the tubular member 920. Patch 944 ensures that bight portion 946 of tensile member or thread 942 is not snagged on possible protuberances inside the endoscope channel.

When loop 926 is ejected from tubular member 920, web member or capture pocket 928 slides along loop 926, staying outside of the tubular member, as illustrated in FIG. 44. In the event that the loop 926 is subsequently ejected again from the distal end of tubular member 920, tensile segments 930 and 932 hold the proximal end of capture pocket 928 so that the pocket slides back along the emerging loop 926 to become repositioned along the loop as illustrated in FIG. 43.

The specific embodiment of the invention illustrated in FIGS. 54 and 55 ensures that the pocket 928 can remain outside the tubular member 920 and yet can be reopened or repositioned in the event it is necessary or desirable to eject the loop 926 again. If tensile segments 930 and 932 were attached to loop 926 or shifting member 924, as it is in some prior art pouches, a polyp contained in capture pocket 928 would be mashed owing to a dragging of the pocket and its contents into tubular member 920.

Figure 45:
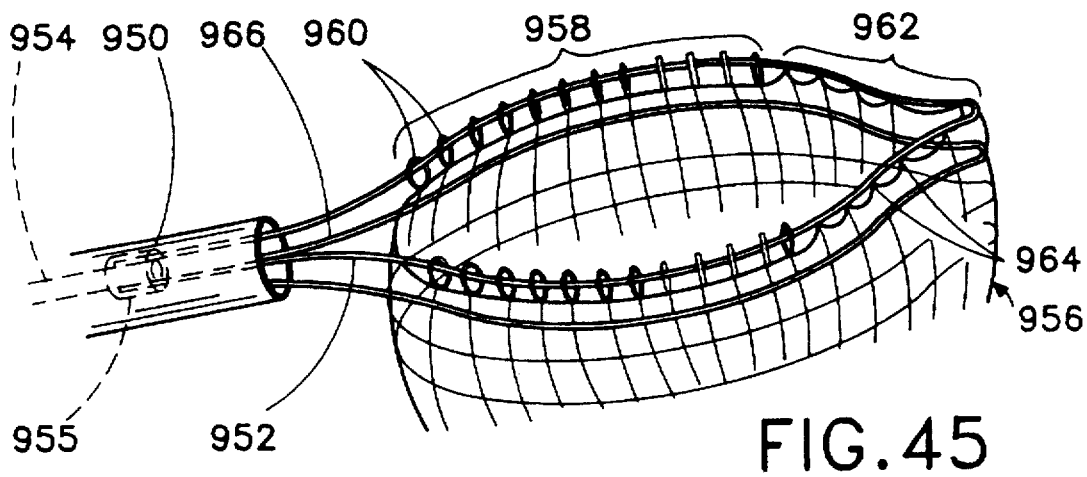
FIG. 45 is a schematic perspective view, on an enlarged scale, of a further capture pocket or pouch in accordance with the present invention, showing the capture pocket or pouch in an opened configuration and attached to a cauterization loop.

As illustrated in FIG. 45, an endoscopic surgical instrument for use in snare cauterization operations comprises a tubular sheath member 950, an alternately expandable and contractible cauterization loop 952, and an electrically conductive wire 954 operatively connected to the loop. Generally, wire 954 is thicker than loop 952 and is crimped thereto at 955 via a swaging procedure.

Wire 954 is slidable longitudinally through sheath member 950, while the sheath is longitudinally insertable through a biopsy channel of an endoscope insertion member (not shown). A flexible web member 956 is connected to loop 952 essentially around a circumference thereof to form a capture pocket, loop 952 defining a mouth opening of the pocket. More specifically, web member 956 is slidably attached to loop 952 along a proximal portion 958 thereof via a plurality of spaced thread ringlets 960. Web member 956 is fixedly but removably attached to loop 952 along a distal portion 962 thereof to enable at least a substantial separation of web member 956 from loop 952 upon a proximally directed cutting stroke of wire 954 during a cauterizing phase of an endoscopic polyp removal operation. As illustrated particularly in FIG. 45, web member 956 is fixed to distal end portion 962 at a plurality of discrete points 964 along a radially outer surface of loop 952. Those attachment points 964 are severable or rupturable, e.g., by the heat of cauterization, so that web member 956 is separated from loop 952 during cauterization.

As further illustrated in FIG. 45, a purse string 966 is attached to web member or pouch 956 along a ring shaped locus proximately to the mouth opening, that is, proximately to loop 952. Purse string 966 is attached at a proximal end to at least one of wire 954 and tubular member 950, as described hereinabove with reference to FIGS. 17, 22, 23, 29A–29C, and 43–44. Purse string 966 is made of a heat-resistant material such as quartz and is attached to wire 954 proximally to the point of connection 955 of loop 952 to wire 954. Because quartz is prone to fracture, it is fixed to wire 954 via a reservoir of adhesive activated by ultraviolet radiation. It is to be noted that the length of purse string 966 must be selected so that the purse string does not close too early during a retraction of loop 952 into tubular sheath member 950. It is to be further noted that the embodiment of FIG. 45 is advantageously provided with the tether 930, 932, 942 of FIG. 43. The tether is omitted in FIG. 45 for purposes of clarity of illustration.

Figure 46:
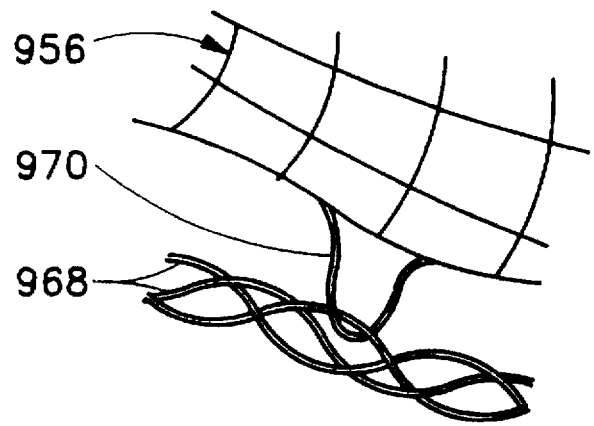
FIG. 46 is a partial schematic perspective view, on a large scale, showing a technique of fastening the capture pocket or pouch of FIG. 45 to the cauterization loop.
Figure 47:
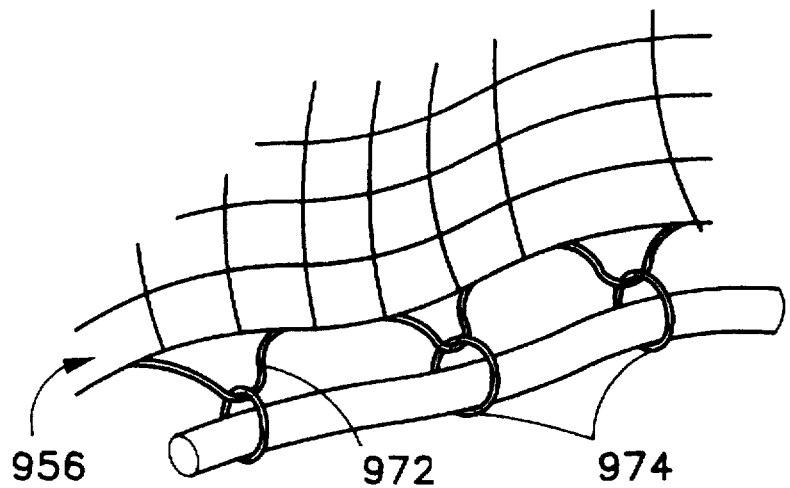
FIG. 47 is a partial schematic perspective view, on a large scale, depicting another technique of attaching the capture pocket or pouch of FIG. 45 to the cauterization loop.

As depicted in FIG. 46, where cauterization loop 952 comprises a plurality of metal strands or filaments 968 wound, woven or braided to one another, web member or capture pouch 956 may be attached to the loop via threads 970 inserted under individual strands or filaments 968 of loop 952. Alternatively, as shown in FIG. 47, web member or capture pouch 956 may be attached to loop 952 via threads 972 and minute metal ringlets 974. Ringlets 974 may become virtually integral with loop 952. In yet another attachment method, indicated in FIG. 48, web member or capture pouch 956 is attached to the radially outer surface of loop 952 along distal portion 962 thereof via an adhesive layer 976. Such an adhesive layer is discussed above in conjunction with FIGS. 17 and 18 et seq.

Generally, it is contemplated that distal portion 962 extends approximately one-third the length of loop 952, while proximal portion 958 extends approximately two-thirds the length of loop 952. Prior to the cutting and cauterizing phase of a polyp removal procedure, thread ringlets 960 slide back and forth along loop 952 as the loop is alternately extended and retracted into tubular sheath member 950 during attempts to properly position loop 952 relative to a polyp. During the cutting and cauterizing phase of the procedure, only distal portion 962 of loop 952 comes into contact with a polyp; the proximal portion 958 is retracted into tubular member 950 prior to the conduction of cauterization current.

The snare assembly of FIGS. 45–48 is designed to solve a problem arising with other snare designs where the web member or pouch is woven onto the cauterization loop. In use, when such a snare closes upon a polyp, the attachment ringlets or threads of the pouch slide towards the distal end of the snare and are interposed between the cauterization loop and the polyp. Thus, the cauterization loop has to cut through the attachment ringlets or threads of the pouch while cutting through the polyp. This may occasionally hinder a polypectomy operation.

Figure 48:
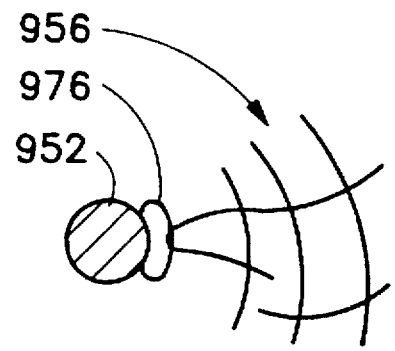
FIG. 48 is a partial schematic cross-sectional view, on a large scale, illustrating yet another technique of attaching the capture pocket or pouch of FIG. 45 to the cauterization loop.

In the design of FIGS. 45, 46 and 48, web member or pouch 956 is attached to loop 952 only along an outer surface thereof at distal portion 962. This attachment of web member or pouch 956 to the cauterization loop 952 cannot interfere with the cutting and cauterizing of a polyp. Where fine metal loops or filaments 974 are used to attach pouch 956 to cauterization loop 952 (FIG. 47), the metal filaments do not interfere with the cauterization process.

The sliding attachment of web member or pouch 956 to proximal portion 958 of cauterization loop 952 enables a repositioning of the snare relative to a polyp. More specifically, after loop 952 has been partially drawn back into tubular member 950, the loop can be shifted again in a distal direction relative to tubular member 950 to enable an adjustment in the position of the snare relative to the polyp. Web member or capture pouch 956 slides along the proximal portion 958 of loop 952 during these adjustments.

Accordingly, in the design of FIGS. 45, 46 and 48, a clean cut is obtained through a polyp, the snare may be repositioned relative to the polyp, and pouch 956 remains outside of tubular member 950 after severing of the polyp. Pouch 956 is severed from cauterization loop 952 during the polypectomy operation. The heat generated during the procedure severs ringlets 960 and releases pouch 956 occurs so that the pouch is held only by purse string 966.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical instrument assembly, comprising:
   a tubular member defining at least one longitudinally extending lumen, said tubular member having a diameter sufficiently small so that said tubular member can be inserted through a biopsy channel of a flexible endoscope;
   a flexible loop having two free ends;
   an elongate flexible shifting member connected at one end to said free ends of said loop, said free ends of said loop and said shifting member being at least partially disposed in said lumen;

a flexible web member connected to said loop so as to form a capture pocket, said web member being movably Attached to said loop so as to slide in a distal direction along said loop during a retraction of said free ends of said loop into said tubular member, thereby closing said pocket; and reopening means for pulling said web member in a proximal direction along said loop during an extension of said loop from said tubular member after said retraction, said reopening means including at least one flexible tensile member connected to said flexible web member and to said tubular member at a point spaced from a distal end thereof, said tensile member extending from said flexible web member into said lumen.

2. The instrument assembly defined in claim 1 wherein said flexible tensile member is one of a plurality of flexible tensile member segments each connected to said flexible web member and to said tubular member, said tensile member segments each extending from said flexible web member into said lumen.

3. The instrument assembly defined in claim 2 wherein said segments are parts of a single flexible tensile member, said tubular member being provided with a pair of holes at about said point, said single flexible tensile member extending through said holes.

4. The instrument assembly defined in claim 3, further comprising a patch disposed on an outer surface of said tubular member over said holes.

5. The instrument assembly defined in claim 1 wherein said web member is slidably connected to said loop at a plurality of spaced locations.

6. A method for removing a selected portion of internal body tissues of a patient, comprising the steps of:

providing a flexible auxiliary loop to which a flexible web member is connected to define an expandable pocket, said auxiliary loop being disposed in a tubular member said auxiliary loop having two free ends fastened to an elongate shifting member at least partially disposed in said tubular member;

inserting an endoscope assembly into a patient;

using said endoscope assembly to visually monitor internal body tissues of the patient after insertion of said endoscope assembly into the patient;

after detecting selected internal body tissues to be removed from the patient, moving said tubular member in a distal direction through a biopsy channel of said endoscope to eject a distal end portion of said tubular member from said biopsy channel;

after ejection of the distal end portion of said tubular member from said biopsy channel, shifting said shifting member, said free ends of said loop and said loop in a distal direction relative to said tubular member to eject said loop from said tubular member;

upon ejection of said loop from said tubular member, at least partially expanding said loop from a collapsed configuration;

manipulating the expanded loop from outside of the patient to pass the expanded loop and the pocket over the selected internal body tissues to be removed;

after a passing of the expanded loop over the selected internal body tissues to be removed, retracting said loop into said tubular member by moving said loop and said free ends of said loop relative to said tubular member;

during the retraction of said loop into said tubular member, sliding said pocket in a distal direction about said loop to at least partially close said pocket to enclose the internal body tissues in said pocket;

subsequently to the retraction of said loop and said free ends of said loop and the closing of said pocket, again shifting said loop in a distal direction relative to said tubular member to eject said loop from said tubular member; and during the shifting of said loop subsequently to the retraction of said loop and the closing of said pocket, pulling said pocket in a proximal direction about said loop to reopen said pocket, thereby enabling a repositioning of said loop and said pocket relative to the selected internal body tissues.

7. The method defined in claim 6 wherein the pulling of said pocket is implemented by a flexible tether member connected to said pocket and to said tubular member.

* * * * *